United States Patent
Fujii et al.

(10) Patent No.: US 10,156,536 B2
(45) Date of Patent: Dec. 18, 2018

(54) GAS SENSOR INCLUDING DETECTION CELLS, AND METHOD FOR DETERMINING HYDROGEN CONCENTRATION

(71) Applicant: Panasonic Intellectual Property Management Co., Ltd., Osaka (JP)

(72) Inventors: Satoru Fujii, Osaka (JP); Kazunari Homma, Kyoto (JP); Zhiqiang Wei, Osaka (JP)

(73) Assignee: PANASONIC INTELLECTUAL PROPERTY MANAGEMENT CO., LTD., Osaka (JP)

( * ) Notice: Subject to any disclaimer, the term of this patent is extended or adjusted under 35 U.S.C. 154(b) by 0 days.

(21) Appl. No.: 15/413,481

(22) Filed: Jan. 24, 2017

(65) Prior Publication Data
US 2017/0241933 A1 Aug. 24, 2017

(30) Foreign Application Priority Data
Feb. 22, 2016 (JP) .................................. 2016-031199

(51) Int. Cl.
*G01N 27/12* (2006.01)
*G01N 33/00* (2006.01)

(52) U.S. Cl.
CPC ......... *G01N 27/125* (2013.01); *G01N 27/128* (2013.01); *G01N 33/005* (2013.01)

(58) Field of Classification Search
CPC ........................... G01N 27/125; G01N 33/005
See application file for complete search history.

(56) References Cited

U.S. PATENT DOCUMENTS

| | | |
|---|---|---|
| 2002/0187075 A1 | 12/2002 | Nadanami et al. |
| 2010/0025241 A1 | 2/2010 | Hane et al. |
| 2013/0000280 A1 | 1/2013 | Korenev |
| 2013/0071986 A1 | 3/2013 | Deweerd et al. |
| 2013/0250658 A1 | 9/2013 | Wei et al. |

FOREIGN PATENT DOCUMENTS

| | | |
|---|---|---|
| JP | 59-058348 | 4/1984 |
| JP | 10-062379 | 3/1998 |
| JP | 2003-240746 | 8/2003 |
| JP | 2003-279522 | 10/2003 |

(Continued)

OTHER PUBLICATIONS

Song, Junghui, et al. "AlGaN/GaN Schottky diode hydrogen sensor performance at high temperatures with different catalytic metals." Solid-state electronics 49.8 (2005): 1330-1334.*

(Continued)

*Primary Examiner* — Robert J Eom
(74) *Attorney, Agent, or Firm* — McDermott Will & Emery LLP

(57) ABSTRACT

A gas sensor includes an insulation layer and detection cells covered with the insulation layer. Each of the plurality of detection cells includes: a first electrode; a second electrode having a surface exposed from the insulation layer; and a metal oxide layer disposed between the first electrode and the second electrode. In each of the detection cells, a resistance value of the metal oxide layer decreases with a response time, which is different in each of the detection cells, when a gas containing a hydrogen atom comes into contact with the second electrodes.

17 Claims, 28 Drawing Sheets

(56) References Cited

FOREIGN PATENT DOCUMENTS

| JP | 2004-061306 | 2/2004 |
| JP | 2004-093389 | 3/2004 |
| JP | 2015-068802 | 4/2015 |
| WO | 2013/051267 | 4/2013 |

OTHER PUBLICATIONS

Luther, B. P., S. D. Wolter, and S. E. Mohney. "High temperature Pt Schottky diode gas sensors on n-type GaN." Sensors and Actuators B: Chemical 56.1-2 (1999): 164-168.*

J. Yu et al., "Hydrogen gas sensing properties of Pt/Ta2O5 Schottky diodes based on Si and SiC substrates", Sensors and Actuators A 172, pp. 9-14, Available online Feb. 25, 2011.

Office Action issued in related U.S. Appl. No. 15/472,429 dated Jul. 26, 2018.

* cited by examiner

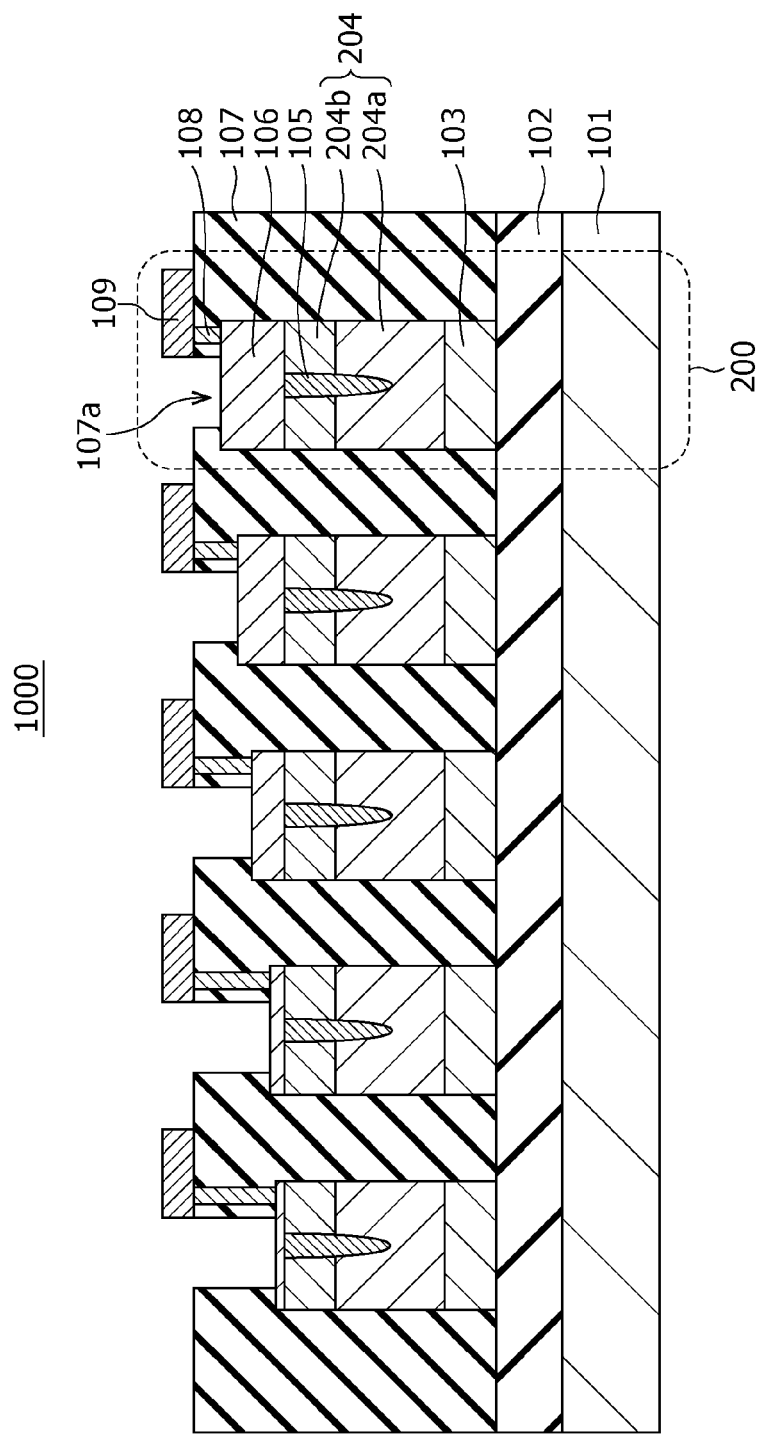

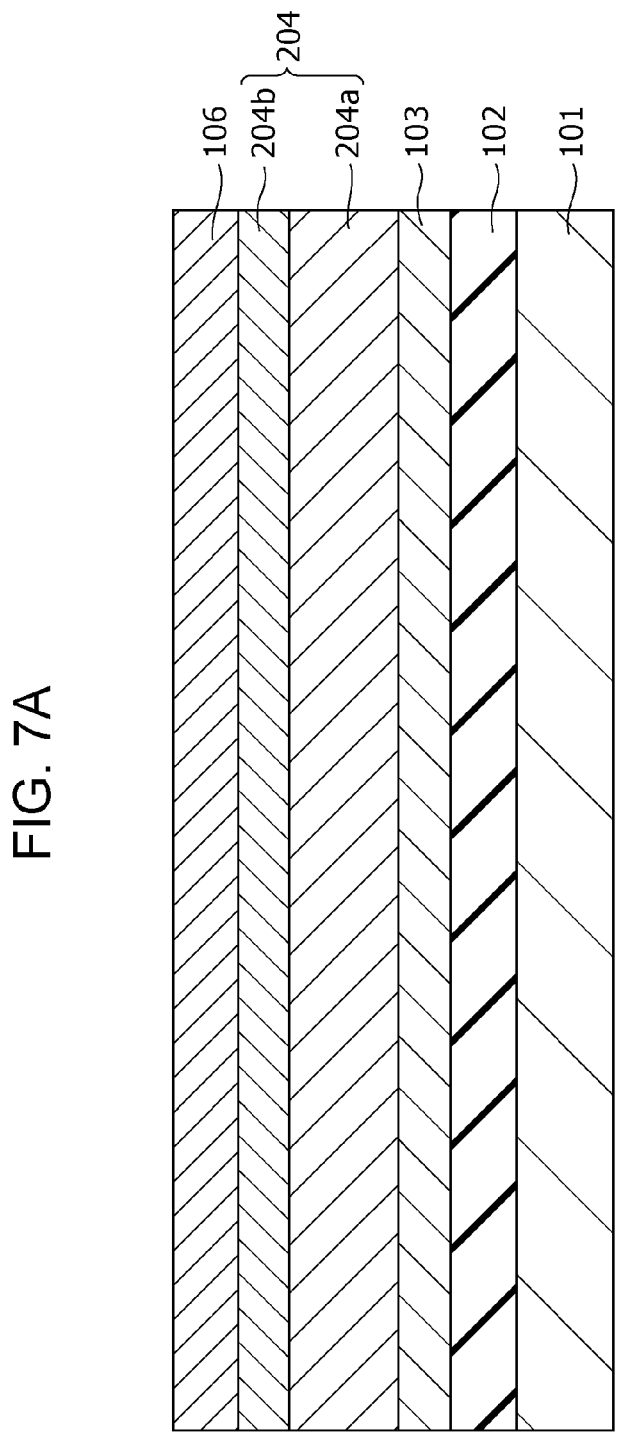

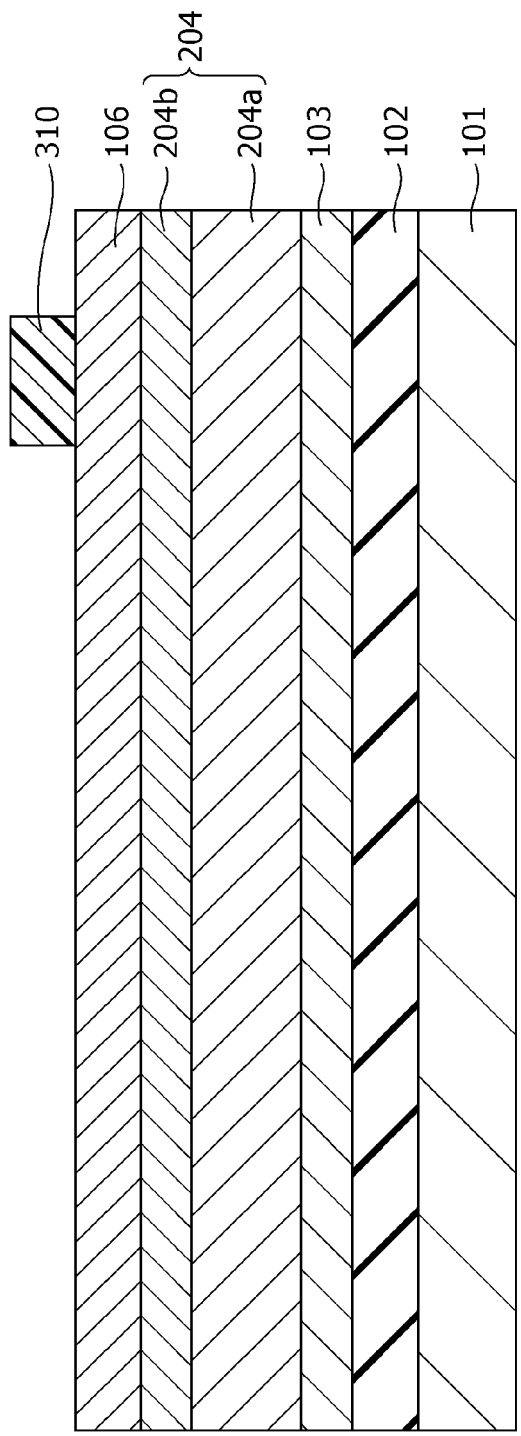

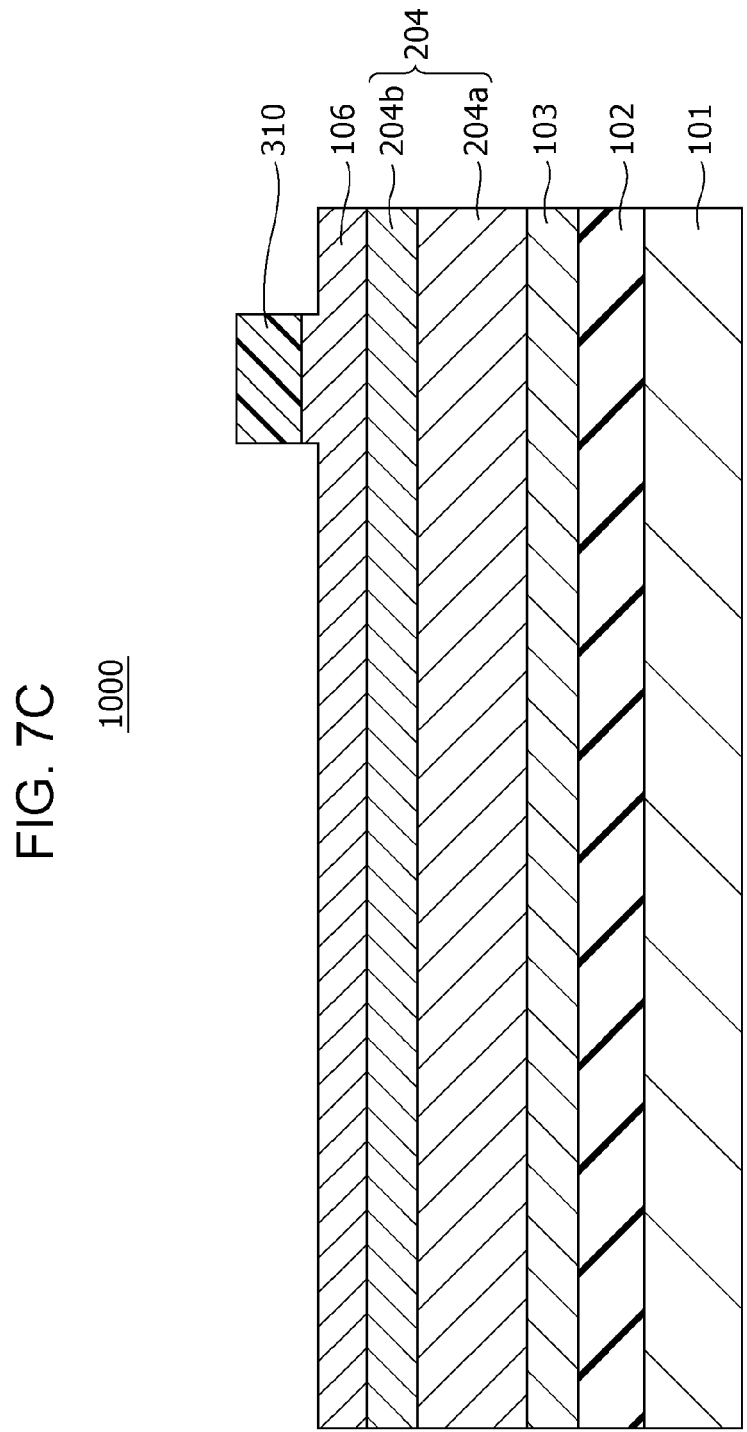

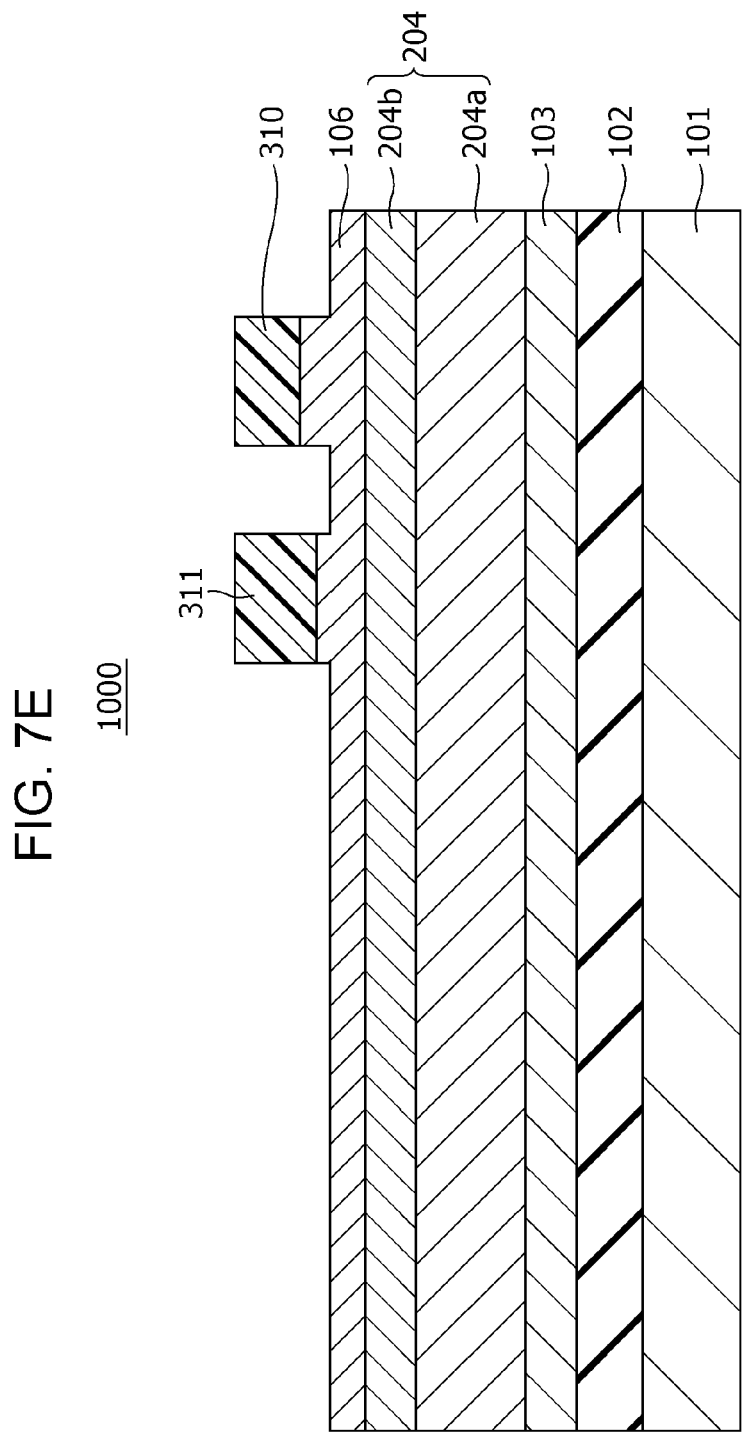

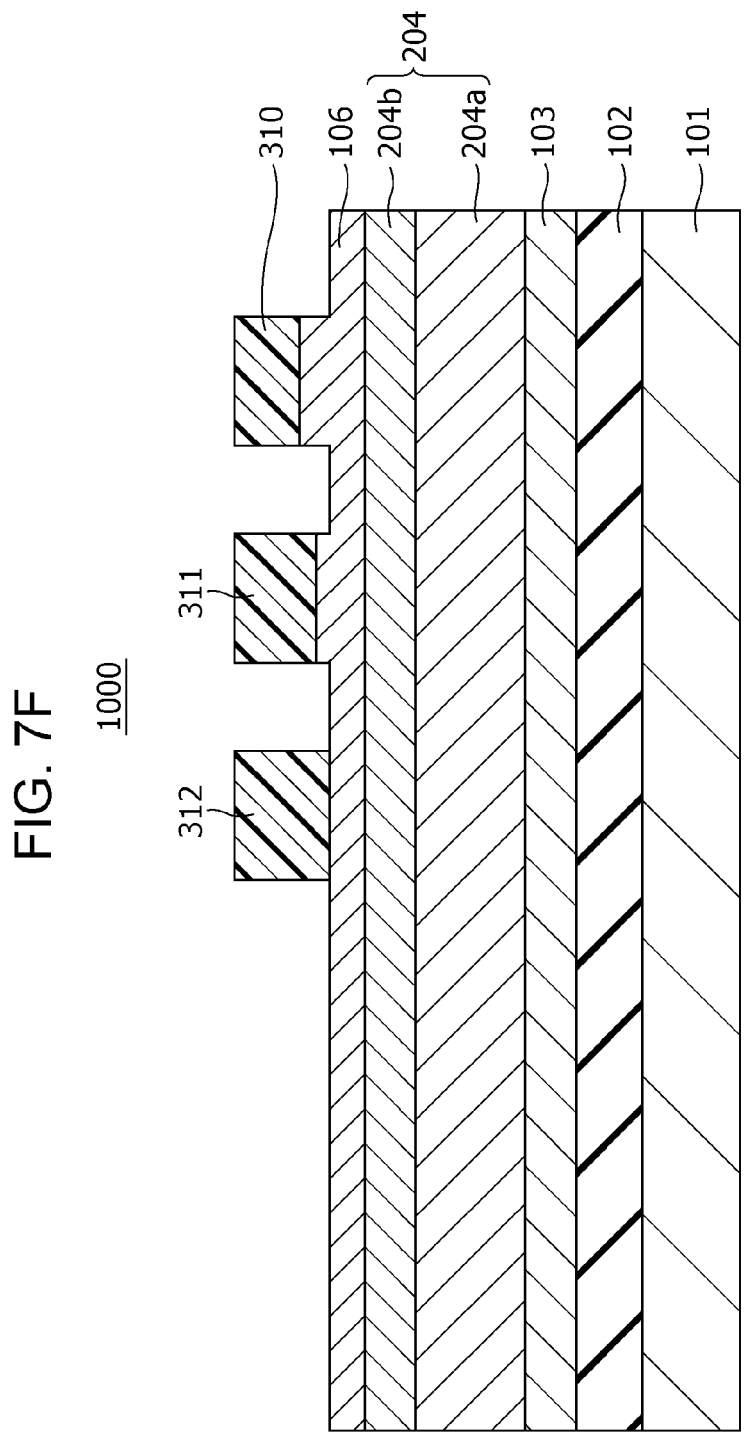

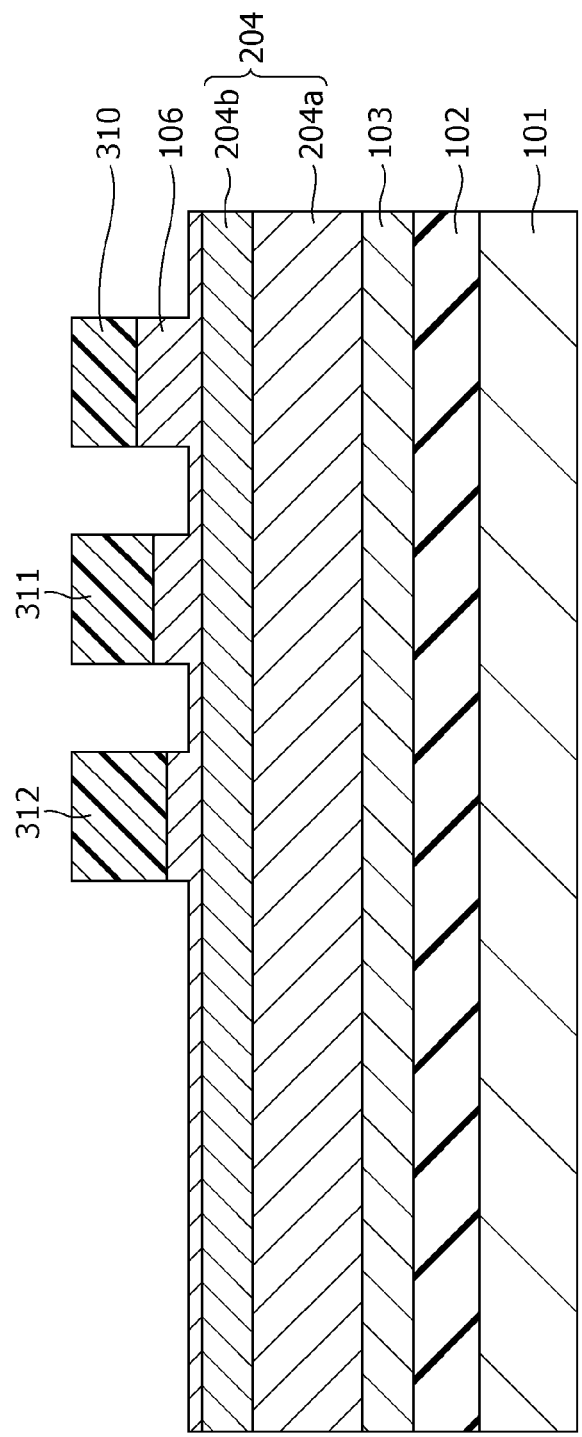

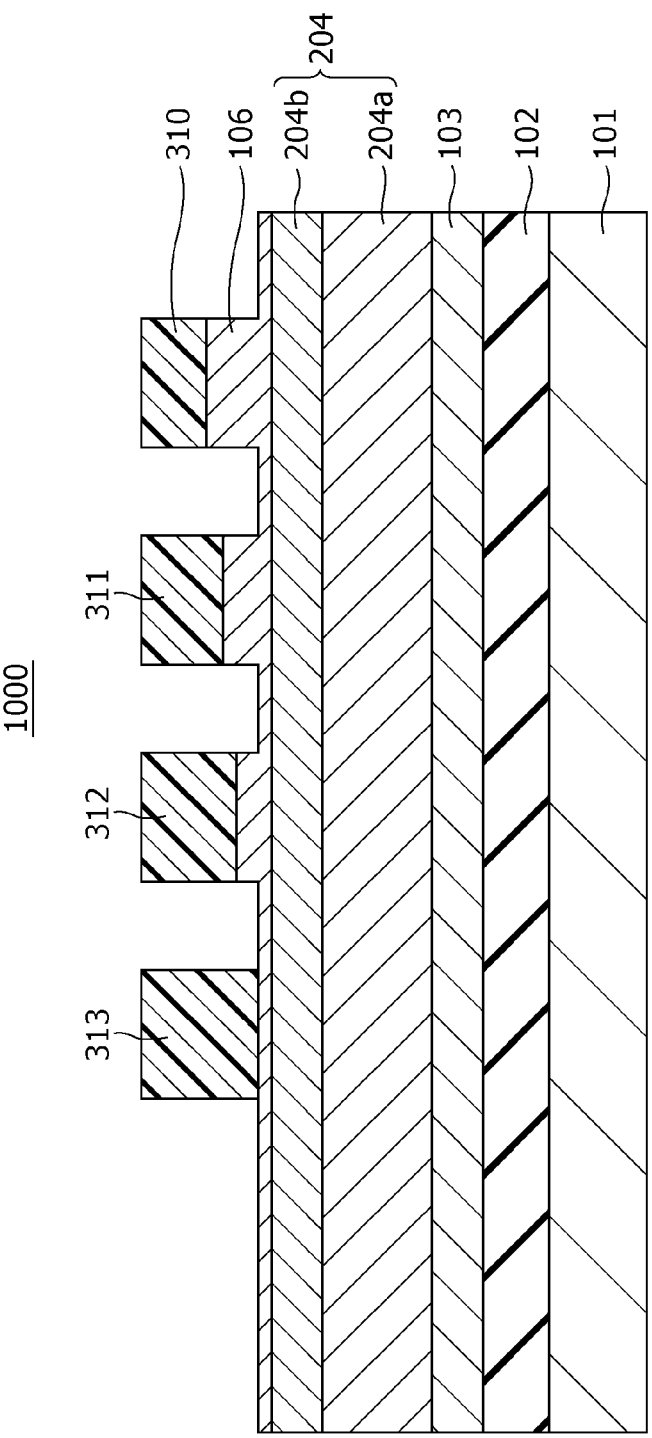

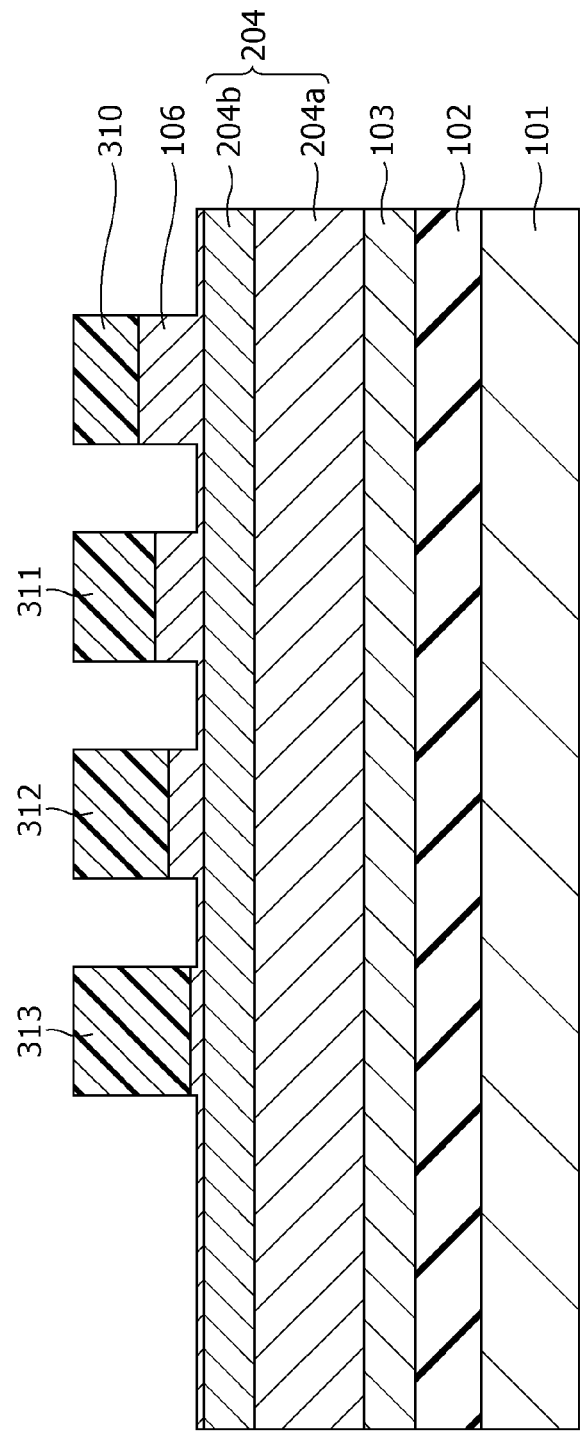

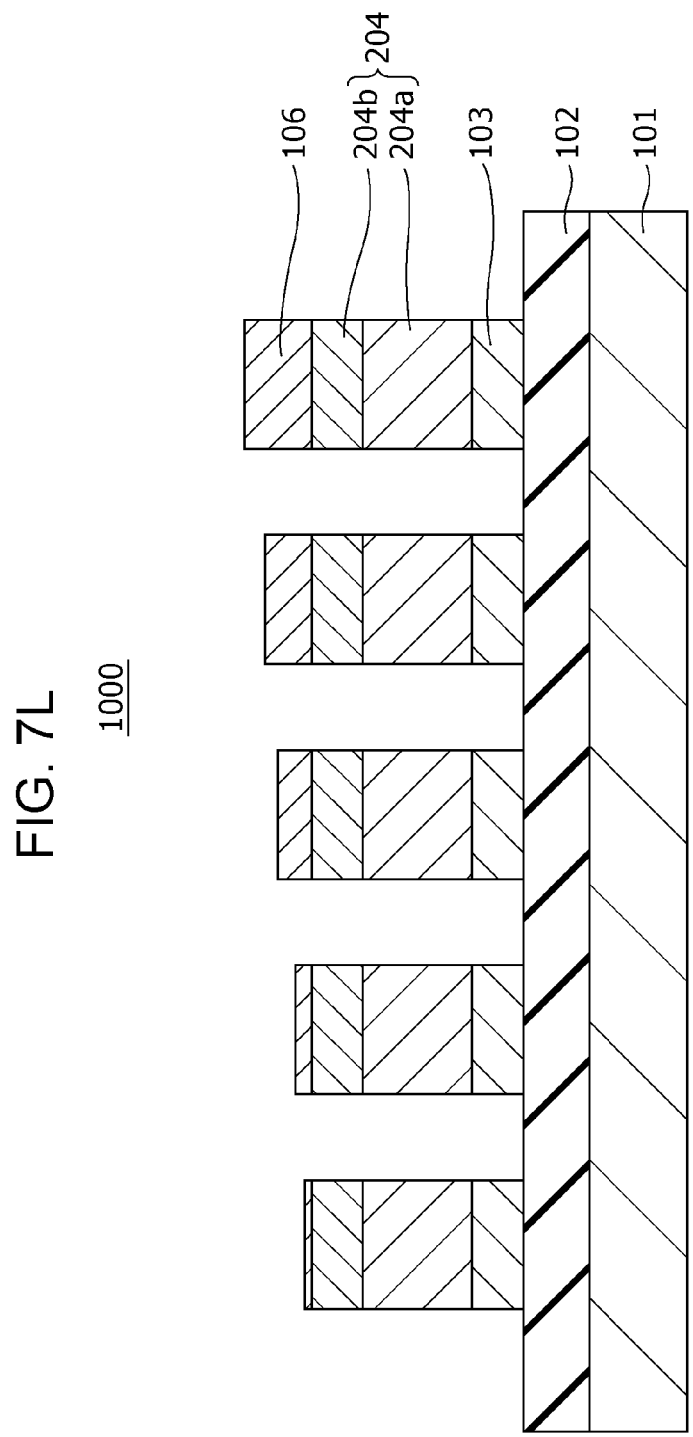

GAS SENSOR INCLUDING DETECTION CELLS, AND METHOD FOR DETERMINING HYDROGEN CONCENTRATION

BACKGROUND

1. Technical Field

The present disclosure relates to a gas sensor and a method for determining a hydrogen concentration by the use of the gas sensor.

2. Description of the Related Art

Japanese Unexamined Patent Application Publication No. 59-58348 discloses a gas sensor for detecting the presence of a hydrogen gas as a variation in a resistance value. The gas sensor includes a material, in which palladium (Pd) and glass are added to tantalum pentoxide ($Ta_2O_5$), and platinum (Pt) electrodes holding the material therebetween.

Sensors and Actuators A: Physical, 172 (2011) pages 9-14 discloses a $Pt/Ta_2O_5$ Schottkey diode for hydrogen sensing. In the Schottkey diode, a hydrogen molecule dissociates into hydrogen atoms on the surface of the catalyst Pt.

SUMMARY

In one general aspect, the techniques disclosed here feature a gas sensor including an insulation layer and detection cells covered with the insulation layer. Each of the detection cells includes: a first electrode; a second electrode having a surface exposed from the insulation layer; and a metal oxide layer disposed between the first electrode and the second electrode, the metal oxide layer including a bulk region and a local region surrounded by the bulk region, a degree of oxygen deficiency of the local region being higher than a degree of oxygen deficiency of the bulk region. In each of the detection cells, a resistance value of the metal oxide layer decreases with a response time, which is different in each of the detection cells, when a gas containing a hydrogen atom comes into contact with the second electrodes.

It should be noted that comprehensive or specific embodiments may be implemented as a system, a method, an integrated circuit, a computer program, a storage medium, or any selective combination thereof.

Additional benefits and advantages of the disclosed embodiments will become apparent from the specification and drawings. The benefits and/or advantages may be individually obtained by the various embodiments and features of the specification and drawings, which need not all be provided in order to obtain one or more of such benefits and/or advantages.

BRIEF DESCRIPTION OF THE DRAWINGS

FIG. 6 is a sectional view showing an example of a gas sensor according to a first embodiment;

FIG. 7A is a sectional view showing an example of a method for manufacturing the gas sensor according to the first embodiment;

FIG. 7B is a sectional view showing an example of the method for manufacturing the gas sensor according to the first embodiment;

FIG. 7C is a sectional view showing an example of the method for manufacturing the gas sensor according to the first embodiment;

FIG. 7E is a sectional view showing an example of the method for manufacturing the gas sensor according to the first embodiment;

FIG. 7F is a sectional view showing an example of the method for manufacturing the gas sensor according to the first embodiment;

FIG. 7G is a sectional view showing an example of the method for manufacturing the gas sensor according to the first embodiment;

FIG. 7H is a sectional view showing an example of the method for manufacturing the gas sensor according to the first embodiment;

FIG. 7I is a sectional view showing an example of the method for manufacturing the gas sensor according to the first embodiment;

FIG. 7L is a sectional view showing an example of the method for manufacturing the gas sensor according to the first embodiment;

DETAILED DESCRIPTION

Figure 1A:
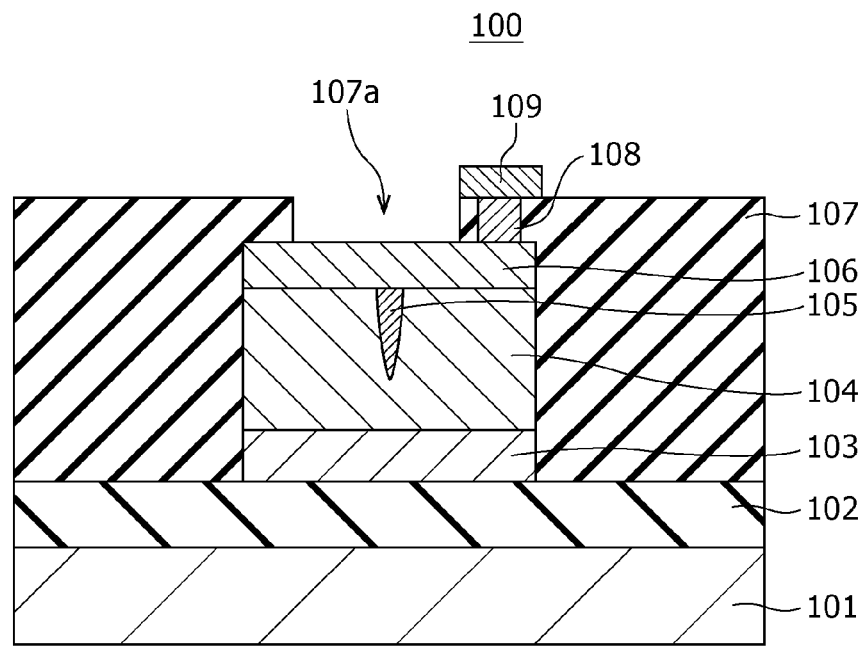
FIG. 1A is a sectional view showing an example of a gas detection element according to a reference embodiment.

The reference embodiment and various embodiments according to the present disclosure will be described below with reference to the drawings.

In the drawings, the same or similar configurations may be represented by the same reference numeral and the explanations of the configurations thereof may be omitted in the specification. The numerical values, materials, shapes, arrangements and connection relationships of constituents, manufacturing methods, and the like described below are examples for specifically explaining the various embodiments, and the present disclosure is not limited to these. Among the constituents exemplified below, the constituents that are not described in the independent claims showing the most significant concepts are explained as optional constituents.

Reference Embodiment

[1. Configuration of Gas Detection Element]

FIG. 1A is a sectional view showing a configuration example of a gas detection element 100 according to a reference embodiment.

Figure 1B:
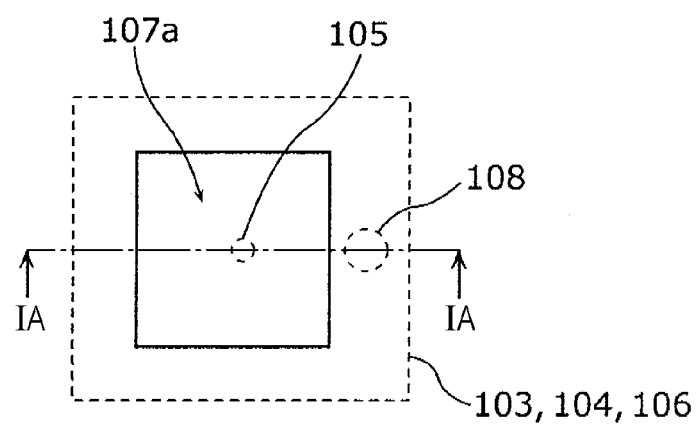
FIG. 1B is a top view showing an example of the gas detection element according to the reference embodiment.

FIG. 1B is a top view showing a configuration example of the gas detection element 100 according to the reference embodiment. The cross section shown in FIG. 1A corresponds to the cross section along a cutting-plane line IA-IA viewed in the direction indicated by the arrows shown in FIG. 1B.

The gas detection element 100 includes a substrate 101, an insulation film 102 disposed on the substrate 101, a first electrode 103 disposed on the insulation film 102, a resistance film 104 disposed on the first electrode 103, a second electrode 106 disposed on the resistance film 104, an insulation film 107 covering the first electrode 103, the resistance film 104, and the second electrode 106, a via 108 connected to the second electrode 106 through the insulation film 107, and a wire 109 connected to the via 108.

In the present disclosure, the "insulation film" is an example of an "insulation layer" and the "resistance film" is an example of a "metal oxide layer".

An opening 107a for bringing the second electrode 106 into contact with a gas, which is a target of inspection, is disposed in the insulation film 107. In other words, at least part of the upper surface of the second electrode 106 is not covered with the insulation film 107 and is exposed from the insulation film 107.

The via 108 penetrates the portion of the insulation film 107, the portion covering the second electrode 106, and is connected to the second electrode 106. The wire 109 is disposed on the via 108.

The resistance film 104 is disposed between the first electrode 103 and the second electrode 106. The resistance value of the resistance film 104 reversibly varies on the basis of an electrical signal applied between the first electrode 103 and the second electrode 106. For example, the resistance film 104 makes an inverse transition between a high resistance state and a low resistance state in accordance with a voltage applied between the first electrode 103 and the second electrode 106 and in accordance with the presence or absence of a hydrogen-containing gas in a gas in contact with the second electrode 106.

The term "hydrogen-containing gas" is a generic name for gases composed of molecules having hydrogen atoms. Examples of hydrogen-containing gases include a hydrogen gas, a methane gas, an alcohol gas, and an ammonia gas.

The thickness of the resistance film 104 may be, for example, 8 nm or less for the purpose of decreasing the initial resistance value or be 1 nm or more for the purpose of obtaining a stable resistance variation.

The resistance film 104 includes a local region 105 which is disposed so as to be in contact with the second electrode 106 and which is not in contact with the first electrode 103. The degree of oxygen deficiency of the local region 105 is larger than the degree of oxygen deficiency of the surroundings thereof (that is, a bulk region of the resistance film 104). The degree of oxygen deficiency of the local region 105 reversibly varies in accordance with application of an electrical signal between the first electrode 103 and the second electrode 106 and in accordance with the presence or absence of a hydrogen-containing gas in a gas in contact with the second electrode 106. The local region 105 is a very small region including filaments (conductive paths) composed of a range of oxygen-deficient sites.

In the present disclosure, the degree of oxygen deficiency of a metal oxide refers to a ratio of the amount of oxygen deficiency of the metal oxide to the amount of oxygen in a stoichiometric metal oxide composed of the same elements as those of the metal oxide (in this regard, the amount of oxygen deficiency is the value obtained by subtracting the amount of oxygen in the metal oxide from the amount of oxygen in the stoichiometric metal oxide). If there are a plurality of stoichiometric metal oxides composed of the same elements as those of the metal oxide, the degree of oxygen deficiency is defined on the basis of the stoichiometric metal oxide having the highest resistance value among those stoichiometric metal oxides. The stoichiometric metal oxide is more stable and has a higher resistance value compared with metal oxides having other compositions.

As an example, the degree of oxygen deficiency of tantalum oxide $TaO_{1.5}$ will be described. The stoichiometric tantalum oxide is $Ta_2O_5$ and, therefore, can be expressed as $TaO_{2.5}$. The degree of oxygen deficiency of $TaO_{2.5}$ is 0%. On the other hand, the degree of oxygen deficiency of $TaO_{1.5}$ is determined to be $(2.5-1.5)/2.5=40\%$.

In the present disclosure, the explanation is made on the assumption that the degree of oxygen deficiency includes a positive value, 0, and a negative value unless otherwise specified. In the case where the degree of oxygen deficiency takes on a positive value, the metal oxide has a composition in which oxygen is deficient. In the case where the degree of oxygen deficiency is 0, the metal oxide has a stoichiometric composition. In the case where the degree of oxygen deficiency takes on a negative value, the metal oxide has a composition in which oxygen is excessive.

In the case where the metal oxide has a composition in which oxygen is deficient, as the degree of oxygen deficiency decreases, the composition of the metal oxide comes close to the stoichiometric composition, and the resistance value thereof increases. Conversely, as the degree of oxygen deficiency increases, the metal oxide becomes more like a metal, and the resistance value thereof decreases.

In the present disclosure, the oxygen content of the metal oxide refers to the ratio of the number of oxygen atoms to the number of total atoms in the metal oxide. For example, the oxygen content of tantalum oxide $Ta_2O_5$ is $5/(2+5)=71.4$ atm %. The oxygen content of an oxygen-deficient tantalum oxide is more than 0 and less than 71.4 atm %.

The local region 105 is formed in the resistance film 104 by applying a predetermined voltage (that is, an initial break voltage) between the first electrode 103 and the second electrode 106. For example, the absolute value of the initial break voltage is larger than the absolute value of the voltage for making an inverse transition of the resistance state of the resistance film 104. Alternatively, the absolute value of the initial break voltage may be smaller than the voltage for making an inverse transition of the resistance state of the resistance film 104. In the latter case, the initial break voltage may be repeatedly applied between the first electrode 103 and the second electrode 106 or be continuously applied for a predetermined period. The local region 105 shown in FIG. 1A is formed by applying the initial break voltage.

The local region 105 may include filaments (conductive paths) composed of a range of oxygen-deficient sites. The local region 105 has a very small size which is commensurate with a filament required for passing a current. Formation of the filament in the local region 105 is explained by using a percolation model.

According to the percolation model, a region of oxygen-deficient sites is easily formed and a filament is formed when the density of oxygen-deficient sites randomly distributed in the local region 105 exceeds a certain threshold value. A resistance variation of the resistance film 104 occurs through appearance and disappearance of oxygen-deficient sites in the local region 105.

The oxygen deficiency of the metal oxide refers to a case where oxygen has been lost from the site which would otherwise have been occupied by oxygen if the metal oxide had a stoichiometric composition. The density of the oxygen-deficient sites corresponds to the degree of oxygen deficiency. That is, as the degree of oxygen deficiency increases, the density of the oxygen-deficient sites increases.

Only one local region 105 may be formed in one resistance film 104 of the gas detection element 100. The local region 105 disposed in the resistance film 104 can be identified on the basis of, for example, electron beam absorbed current (EBAC) analysis.

The resistance film 104 includes the local region 105. Therefore, when a voltage is applied between the first electrode 103 and the second electrode 106, a current intensively passes through the local region 105 in the resistance film 104.

The diameter of the local region 105 is very small. Therefore, for example, if several tens of microamperes of current passes through the local region 105 by applying about 1 V of voltage, a marked temperature increase (for example, a temperature increase larger than 100° C.) of the local region 105 occurs. Therefore, the local region 105 and the surrounding area can be heated by a small power consumption (for example, less than 0.1 mW).

For example, the portion, which is in contact with the local region 105, of the second electrode 106 is heated because of heat generation of the local region 105. Therefore, in the case where the second electrode 106 is a metal (for example, Pt) having a catalytic effect, the catalytic effect is enhanced because of the heating, and the efficiency of dissociation of hydrogen atoms from a hydrogen-containing gas increases.

It is estimated that the dissociated hydrogen atoms vary the resistance value of the resistance film 104 under the mechanism described below.

The dissociated hydrogen atoms diffuse into the second electrode 106 and reach the local region 105 so as to maintain a state of equilibrium. These hydrogen atoms bond to oxygen atoms in the local region 105 so as to form water molecules. Consequently, the degree of oxygen deficiency in the local region 105 increases, filaments are easily connected to each other and the resistance value of the local region 105 decreases. As a result, a current that passes between the first electrode 103 and the second electrode 106 increases.

On the other hand, if a hydrogen-containing gas is not present in the vicinity of the second electrode 106, dissociated hydrogen atoms form hydrogen molecules in the vicinity of the surface of the second electrode 106 so as to maintain a state of equilibrium and go to the outside from the surface of the second electrode 106. At this time, hydrogen atoms constituting water molecules return to the second electrode 106 from the local region 105, and residual oxygen atoms return to oxygen-deficient sites in the local region 105. Consequently, the degree of oxygen deficiency in the local region 105 decreases, filaments are not easily connected to each other, and the resistance value increases. As a result, a current that passes between the first electrode 103 and the second electrode 106 decreases.

As described above, the gas detection element 100 has a feature that when the second electrode 106 comes into contact with a hydrogen-containing gas, the resistance value of the resistance film 104 decreases, and when the second electrode 106 comes off the hydrogen-containing gas, the resistance value of the resistance film 104 increases. Consequently, the gas detection element 100 can detect the presence or absence of a hydrogen-containing gas on the basis of the resistance value between the first electrode 103 and the second electrode 106.

A decrease in the resistance value due to a hydrogen-containing gas may occur in the case where the local region 105 is in a high resistance state and also in the case where the local region 105 is in a low resistance state. Consequently, the local region 105 may be set to be in either the high resistance state or the low resistance state. In the case where the local region 105 is set to be in the high resistance state, a decrease in the resistance value can be more clearly detected.

The gas detection element 100 will be described below in detail.

The resistance film 104 is composed of, for example, an oxygen-deficient metal oxide. The base metal of the metal oxide may be one selected from transition metals, e.g., tantalum (Ta), hafnium (Hf), titanium (Ti), zirconium (Zr), niobium (Nb), tungsten (W), nickel (Ni), and iron (Fe), and aluminum (Al). The transition metal can take a plurality of oxidation states and, therefore, the resistance state thereof can vary depending on an oxidation-reduction reaction.

Most of oxygen-deficient metal oxides typically have semiconductor-like characteristics. A resistance variation stably occurs with good reproducibility in the gas detection element 100 by using the oxygen-deficient metal oxide as the resistance film 104.

For example, in the case where the resistance film 104 is composed of a hafnium oxide $HfO_x$, x may be 1.6 or more. Consequently, the resistance value of the resistance film 104 can vary stably. The film thickness of the hafnium oxide may be, for example, 3 to 4 nm.

For example, in the case where the resistance film 104 is composed of a zirconium oxide $ZrO_x$, x may be 1.4 or more. Consequently, the resistance value of the resistance film 104 can vary stably. The film thickness of the zirconium oxide may be, for example, 1 to 5 nm.

For example, in the case where the resistance film 104 is composed of a tantalum oxide $TaO_x$, x may be 2.1 or more. Consequently, the resistance value of the resistance film 104 can vary stably.

The composition of the metal oxide of the resistance film 104 may be measured by using Rutherford backscattering spectrometry.

The material for forming each of the first electrode 103 and the second electrode 106 may be one selected from, for example, platinum (Pt), iridium (Ir), palladium (Pd), silver (Ag), nickel (Ni), tungsten (N), copper (Cu), aluminum (Al), tantalum (Ta), titanium (Ti), titanium nitride (TiN), tantalum nitride (TaN), and titanium aluminum nitride (TiAlN).

The second electrode 106 may be composed of, for example, platinum (Pt), iridium (Ir), or palladium (Pd). These materials have a catalytic effect of dissociating hydrogen atoms from a hydrogen-containing gas. The first electrode 103 may be composed of, for example, tungsten (W), nickel (Ni), tantalum (Ta), titanium (Ti), aluminum (Al), tantalum nitride (TaN), or titanium nitride (TiN). The standard electrode potentials of these materials are lower than the standard electrode potential of the metal contained in the resistance film 104. As the value of the standard electrode potential increases, the material is not easily oxidized.

For example, a silicon single-crystal substrate or a semiconductor substrate can be used as the substrate 101, but the substrate 101 is not limited to these. The resistance film 104 can be formed at a relatively low substrate temperature and, therefore, the resistance film 104 can be formed on, for example, a resin material.

The gas detection element 100 may further include a load element electrically connected to the resistance film 104. Examples of load elements include a solid resistor, a transistor, and a diode.

[2. Method for Manufacturing Gas Detection Element]

An example of the method for manufacturing the gas detection element 100 will be described below with reference to FIGS. 2A to 2G.

Figure 2A:
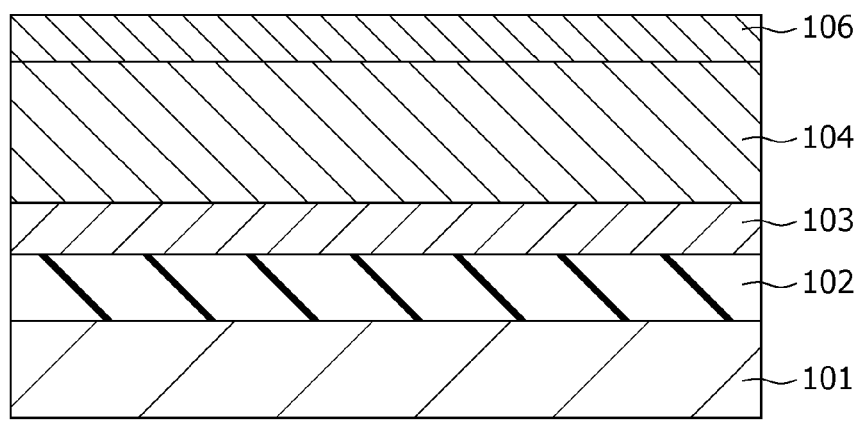
FIG. 2A is a sectional view showing an example of a method for manufacturing the gas detection element according to the reference embodiment.

As shown in FIG. 2A, the insulation film 102, the first electrode 103, the resistance film 104, and the second electrode 106 are formed in this order on the substrate 101.

For example, the substrate 101 is a silicon single-crystal substrate, the insulation film 102 is a silicon thermal oxidation film having a thickness of 200 nm, the first electrode 103 is a Pt thin film having a thickness of 100 nm, the resistance film 104 is an oxygen-deficient tantalum oxide thin film having a thickness of 1 nm or more and 8 nm or less, and the second electrode 106 is a Pt thin film having a thickness of 150 nm.

In this case, the insulation film 102 is formed on the substrate 101 by a thermal oxidation method. The first electrode 103 is formed on the insulation film 102 by a sputtering method. The resistance film 104 is formed on the first electrode 103 by a reactive sputtering method. The second electrode 106 is formed on the resistance film 104 by the sputtering method. In this regard, an adhesion layer composed of Ti, TiN, or the like may be formed between the first electrode 103 and the insulation film 102 by the sputtering method.

Figure 2B:
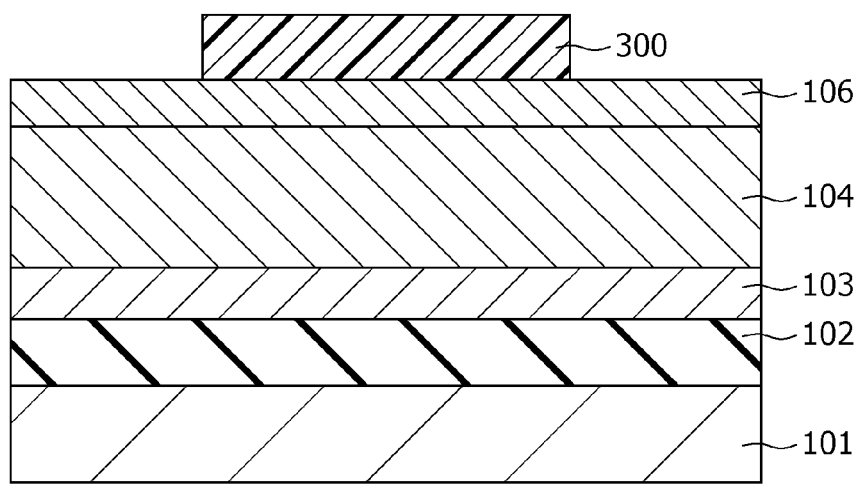
FIG. 2B is a sectional view showing an example of a method for manufacturing the gas detection element according to the reference embodiment.

As shown in FIG. 2B, a mask 300 composed of a photoresist is formed by photolithography.

Figure 2C:
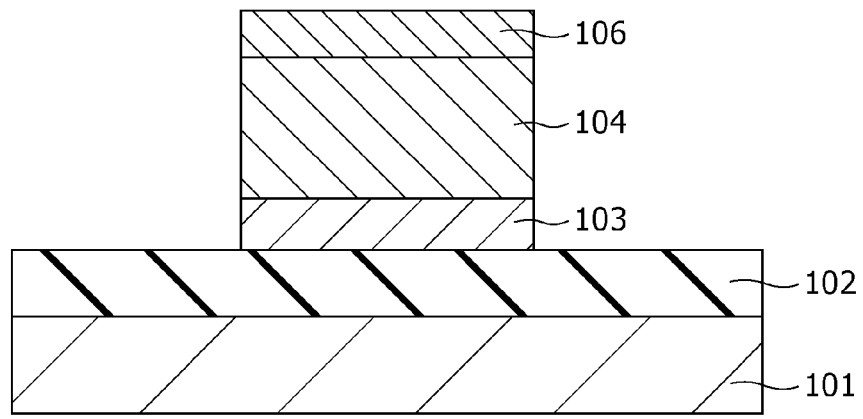
FIG. 2C is a sectional view showing an example of a method for manufacturing the gas detection element according to the reference embodiment.

As shown in FIG. 2C, the first electrode 103, the resistance film 104, and the second electrode 106 are processed so as to have a predetermined shape by dry etching by the use of the mask 300.

Figure 2D:
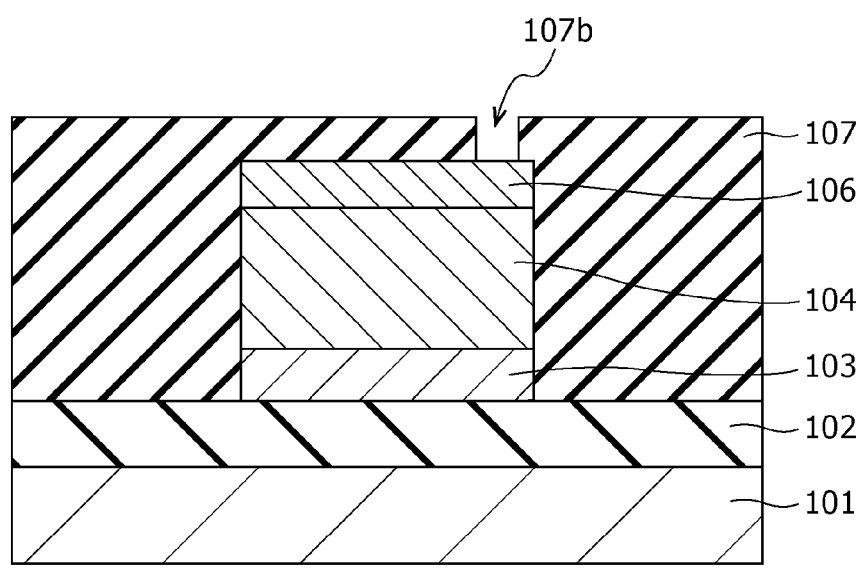
FIG. 2D is a sectional view showing an example of a method for manufacturing the gas detection element according to the reference embodiment.

As shown in FIG. 2D, an insulation film 107 is formed so as to cover the insulation film 102, the first electrode 103, the resistance film 104, and the second electrode 106. Subsequently, a via hole 107b, which reaches part of the upper surface of the second electrode 106, is formed in the insulation film 107 by etching.

Figure 2E:
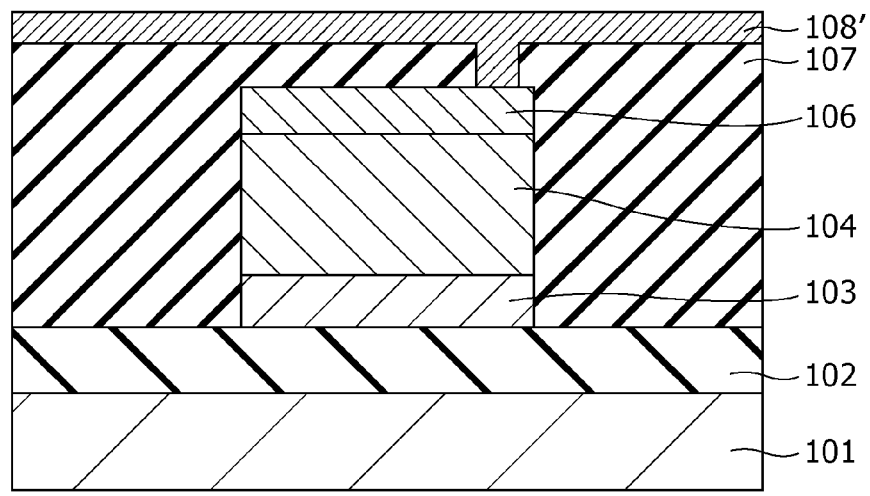
FIG. 2E is a sectional view showing an example of a method for manufacturing the gas detection element according to the reference embodiment.

As shown in FIG. 2E, a conductor film 108' is formed on the upper surface of the insulation film 107 and in the via hole 107b.

Figure 2F:
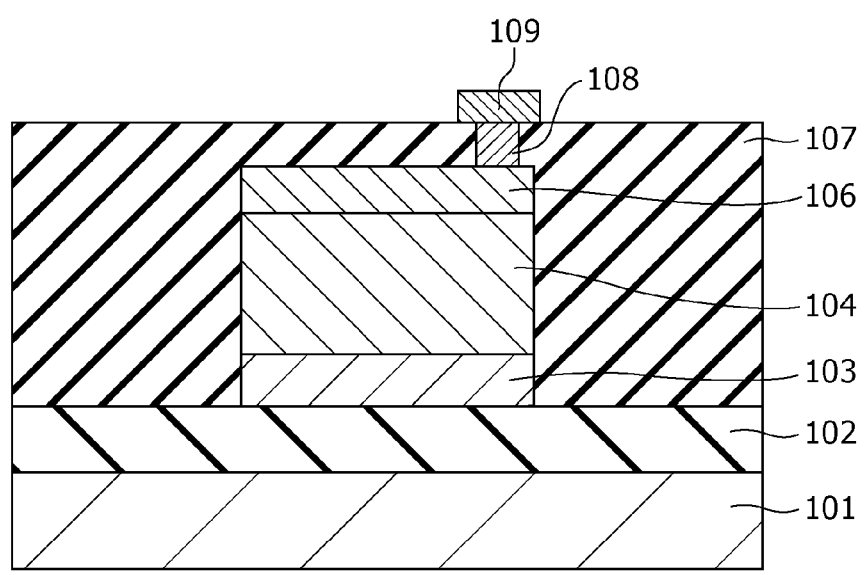
FIG. 2F is a sectional view showing an example of a method for manufacturing the gas detection element according to the reference embodiment.

As shown in FIG. 2F, the conductor film 108' on the insulation film 107 is removed by chemical mechanical polishing (CMP) so as to form a via 108 in the via hole 107b. Then, a new conductor film is formed on the insulation film 107 and is patterned so as to form a wire 109.

Figure 2G:
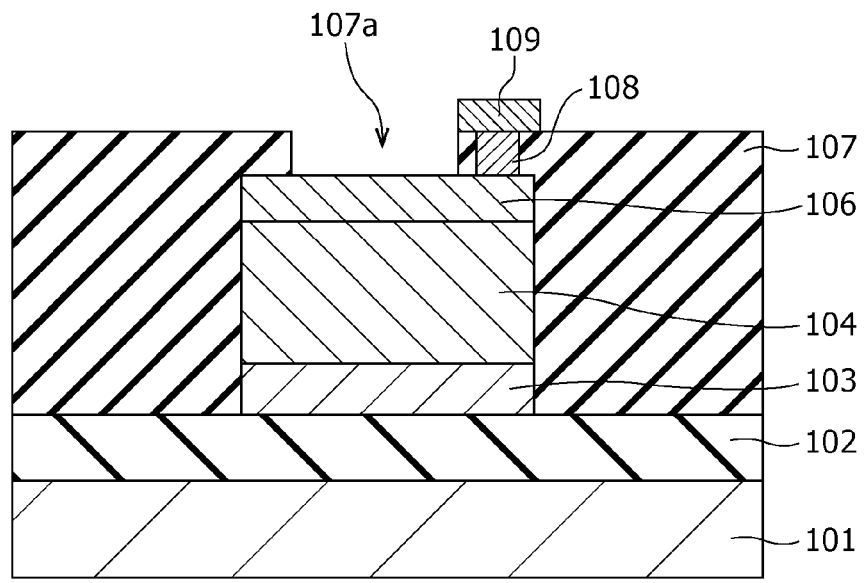
FIG. 2G is a sectional view showing an example of a method for manufacturing the gas detection element according to the reference embodiment.

As shown in FIG. 2G, an opening is made in the insulation film 107 by etching. Part of the upper surface of the second electrode 106 is exposed from the insulation film 107 in the opening 107a.

An initial break voltage is applied between the first electrode 103 and the second electrode 106 so as to form the local region 105 in the resistance film 104, as shown in FIG. 1A. The gas detection element 100 is completed through the above-described steps.

[3. Resistance Variation Due to Application of Voltage]

An example of resistance variation characteristics of the gas detection element 100 in accordance with application of the voltage will be described. In this regard, resistance variation characteristics of the gas detection element 100 in accordance with the hydrogen-containing gas will be described later.

The resistance value was measured by using a sample of the gas detection element 100.

In the sample, the size of each of the first electrode 103, the second electrode 106, and the resistance film 104 was 0.5 μm×0.5 μm (area of 0.25 μm$^2$). The material for forming the resistance film 104 was tantalum oxide TaO$_{2.47}$. The thickness of the resistance film 104 was 5 nm.

The resistance value of the sample was read by applying a reading voltage of 0.4 V between the first electrode 103 and the second electrode 106.

Figure 3:
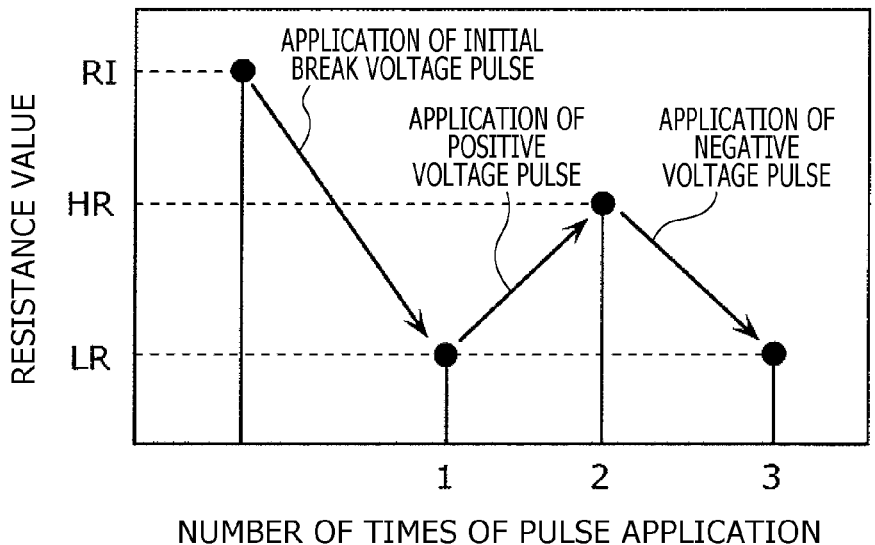
FIG. 3 is a diagram showing an example of a state transition of the gas detection element according to the reference embodiment.

FIG. 3 shows the resistance variation characteristics of the sample of the gas detection element 100.

The initial resistance value RI of the sample was about 107 to 108Ω. An initial break voltage was applied to the sample. As a result, the resistance value decreased, as shown in FIG. 3. Thereafter, two types of voltage pulses having a pulse width of 100 ns and different polarities were alternately applied to the sample. As a result, the resistance value reversibly varied, as shown in FIG. 3.

Specifically, when a positive voltage pulse (pulse width of 100 ns) was applied to the sample, the resistance value increased from a low resistance value LR to a high resistance value HR. On the other hand, when a negative voltage pulse (pulse width of 100 ns) was applied to the sample, the resistance value decreased from the high resistance value HR to the low resistance value LR. The polarity of the voltage pulse was specified as "positive" in the case where the potential of the second electrode 106 was high relative to the potential of the first electrode 103 and was specified as "negative" in the case where the potential of the second electrode 106 was low relative to the potential of the first electrode 103.

The resistance state of the resistance film 104 can be set to be a predetermined resistance state before detection of a hydrogen-containing gas is started by using such resistance variation characteristics in accordance with application of the voltage. For example, the resistance film 104 may be set to be in a high resistance state by applying a positive voltage pulse between the first electrode 103 and the second electrode 106. Consequently, a decrease in the resistance value can be detected more clearly, and the detection characteristics with respect to the hydrogen-containing gas are enhanced.

[4. Modified Example of Configuration of Gas Detection Element]

Figure 4:
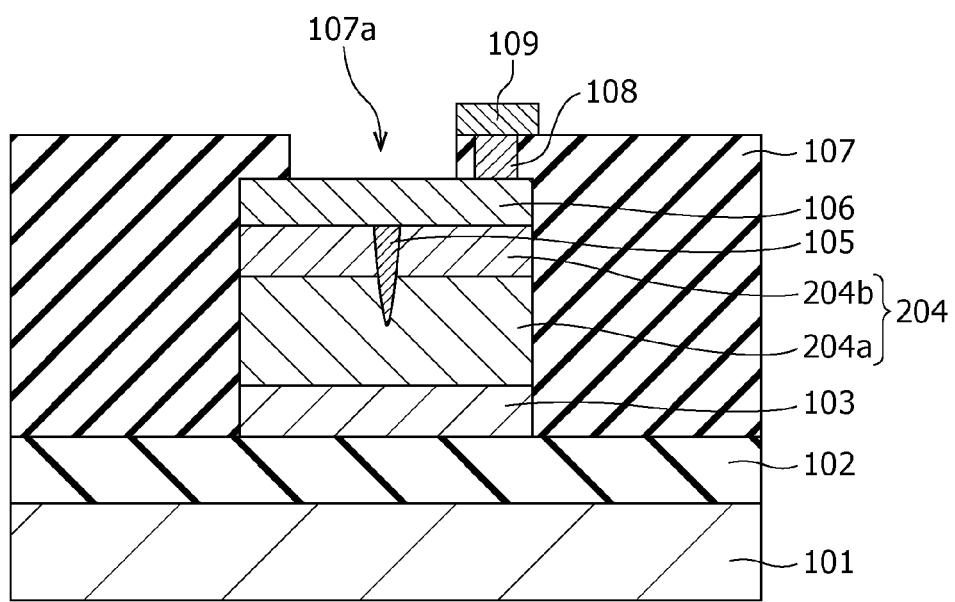
FIG. 4 is a sectional view showing a gas detection element according to a modified example of the reference embodiment.

FIG. 4 is a sectional view schematically showing the configuration of a gas detection element according to a modified example of the reference embodiment. Only the point different from the gas detection element 100 according to the reference embodiment will be described below.

The gas detection element 200 according to the present modified example is different from the gas detection element 100 from the view point that the resistance film 204 is a multilayer body. Specifically, the resistance film 204 includes a first metal oxide layer 204a in contact with the first electrode 103 and a second metal oxide layer 204b in contact with the second electrode 106. The metal oxide layers are not limited to two layers, and the resistance film 204 may be formed by stacking at least three layers of metal oxide layers.

The local region 105 is disposed in each of the first metal oxide layer 204a and the second metal oxide layer 204b. The local region 105 penetrates the second metal oxide layer 204b. The local region 105 is in contact with the second electrode 106 and is not in contact with the first electrode 103.

The thickness of the second metal oxide layer 204b may be smaller than the thickness of the first metal oxide layer 204a. In this case, the structure in which the local region 105 is not in contact with the first electrode 103 can be easily formed. The degree of oxygen deficiency of the second metal oxide layer 204b may be lower than the degree of oxygen deficiency of the first metal oxide layer 204a. In this case, the resistance value of the second metal oxide layer 204b is larger than the resistance value of the first metal oxide layer 204a and, therefore, most of the voltage applied to the resistance film 204 is applied to the second metal oxide layer 204b. Consequently, for example, the local region 105 can be formed in the second metal oxide layer 204b at a low initial break voltage.

The metal constituting the first metal oxide layer 204a may be the same as or different from the metal constituting the second metal oxide layer 204b.

In the case where the metal constituting the first metal oxide layer 204a is the same as the metal constituting the second metal oxide layer 204b, there is a correspondence between the oxygen content and the degree of oxygen deficiency. That is, when the oxygen content of the second metal oxide is larger than the oxygen content of the first metal oxide, the degree of oxygen deficiency of the second metal oxide is lower than the degree of oxygen deficiency of the first metal oxide.

The degree of oxygen deficiency of the local region 105 is higher than the degree of oxygen deficiency of the second metal oxide layer 204b and is different from the degree of oxygen deficiency of the first metal oxide layer 204a.

5. Resistance Variation Due to Hydrogen-Containing Gas

An example of resistance variation characteristics of the gas detection element 200 in accordance with the hydrogen-containing gas will be described. A variation in the resistance value was measured by using a sample of the gas detection element 200.

Figure 5A:
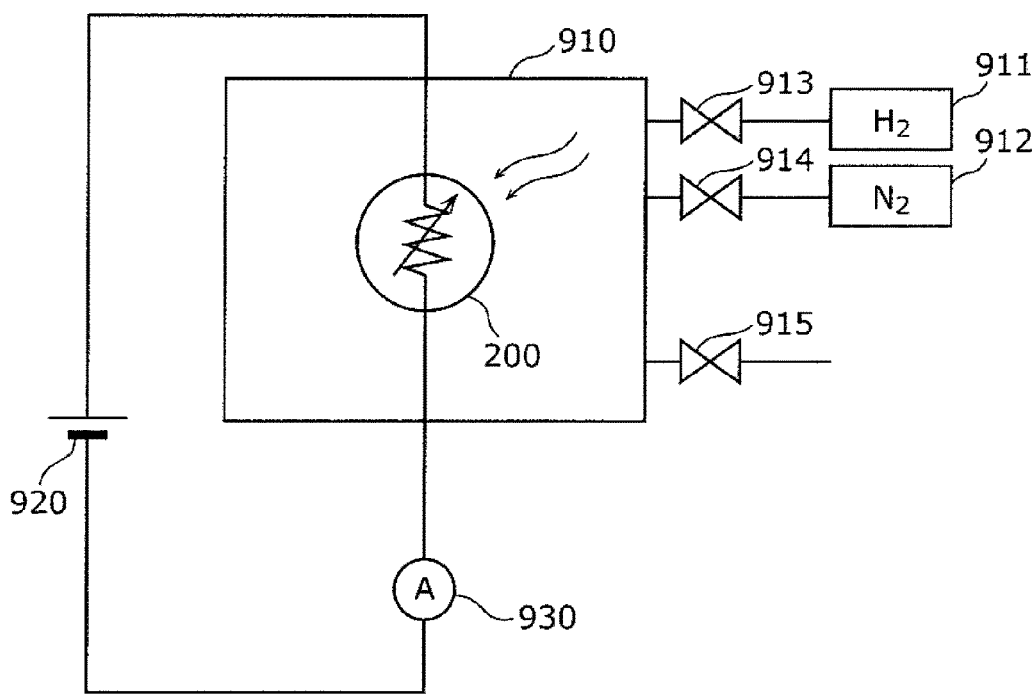
FIG. 5A is a diagram showing an evaluation system of the gas detection element according to the modified example of the reference embodiment.

FIG. 5A is a block diagram showing an example of an evaluation system used for evaluating the gas detection element 200. An evaluation system 900 shown in FIG. 5A includes a closed container 910 for accommodating the gas detection element 200, a power supply circuit 920, and a current measuring instrument 930. The closed container 910 is connected to a hydrogen gas cylinder 911 through an introduction valve 913, is connected to a nitrogen gas cylinder 912 through an introduction valve 914, and is connected to an external space through an exhaust valve 915.

Figure 5B:
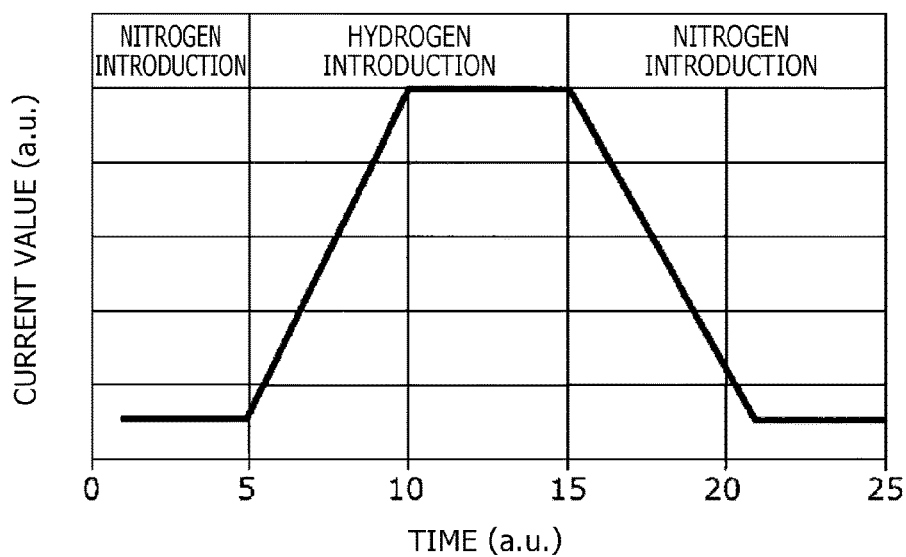
FIG. 5B is a diagram showing an evaluation result of the gas detection element according to the modified example of the reference embodiment.

FIG. 5B shows resistance variation characteristics of the sample of the gas detection element 200. The horizontal axis indicates the time (a.u.) and the vertical axis indicates the value (a.u.) of a current that passes between the first electrode 103 and the second electrode 106.

In the present measurement, the sample of the gas detection element 200 was prepared. The resistance film 204 of the sample was set to be in the high resistance state by applying a voltage. The sample was accommodated into the closed container 910. Thereafter, a detection voltage of 0.6 V was continuously applied between the electrodes of the sample and a current passing through the sample was monitored. Initially, a nitrogen gas was introduced into the closed container 910. Subsequently, introduction of the nitrogen gas was stopped, and a hydrogen gas was introduced into the closed container 910. Then, introduction of the hydrogen gas was stopped, and the nitrogen gas was introduced into the closed container 910 again.

As shown in FIG. 5B, the current value began to increase after the introduction gas was switched from the nitrogen gas to the hydrogen gas. The current value began to decrease after the introduction gas was switched from the hydrogen gas to the nitrogen gas.

A current of 10 to 20 μA passed between the first electrode 103 and the second electrode 106 during introduction of the hydrogen gas. Therefore, according to the sample, the presence or absence of a hydrogen-containing gas could be detected with a very small power consumption of 0.006 to 0.012 mW.

From the above-described measurement results, it was shown that the gas detection element 200 could detect the hydrogen-containing gas. According to the present measurement results, it is estimated that a gas detection element (for example, the gas detection element 100) having a structure similar to the gas detection element 200 exhibits the same resistance variation.

First Embodiment

A gas sensor according to a first embodiment will be described. Regarding the explanations of the first embodiment, the same explanations as those of the reference embodiment may be omitted.

[1. Configuration of Gas Sensor]

FIG. 6 is a sectional view showing a configuration example of a gas sensor 1000 according to the first embodiment. The gas sensor 1000 includes a plurality of gas detection elements 200 as detection cells. Each of the plurality of gas detection elements 200 has, for example, the same structure as the structure of the gas detection element 200 explained in the reference embodiment. In the gas sensor 1000 shown in FIG. 6, five gas detection elements 200 are arranged. The film thicknesses of the second electrodes 106 of the five gas detection elements 200 are different from each other.

The number of the gas detection elements 200 included in the gas sensor 1000 is not limited to five. The gas sensor 1000 may include, for example, a plurality of gas detection elements 100 described in the reference embodiment in place of the plurality of gas detection elements 200. Each of the substrates 101 and the insulation film 102 in the gas sensor 1000 may be common to the plurality of gas detection elements 200. Likewise, the insulation film 107 of the gas sensor 1000 may be a common layer covering the plurality of first electrodes 103, the plurality of resistance films 204, and the plurality of second electrodes 106 of the plurality of gas detection elements 200.

In FIG. 6, all the film thicknesses of the second electrodes 106 of five gas detection elements 200 are different from each other. However, at least two of film thicknesses of the second electrodes 106 of the plurality of gas detection elements 200 may be different from each other. For example, the film thickness of the second electrode 106 having the maximum film thickness among the plurality of gas detection elements 200 may be 1.5 or more times the film thickness of the second electrode 106 having the minimum film thickness.

[2. Method for Manufacturing Gas Sensor]

Regarding a method for manufacturing the gas sensor 1000, basically, the same manufacturing method as the manufacturing method explained with reference to FIG. 2A to FIG. 2G may be used. However, in the method for manufacturing the gas sensor 1000, in order to make the film thicknesses of the second electrodes 106 different in every gas detection element 200, a plurality of times of etching steps are added.

Theses etching steps are shown in FIG. 7A to FIG. 7L.

As shown in FIG. 7A, the substrate 101, the insulation film 102, the first electrode 103, the resistance film 204, and the second electrode 106 are stacked in this order. The manufacturing method and the material for each layer may be, for example, the same as those explained with reference to FIG. 2A.

As shown in FIG. 7B, a mask 310 is formed on the second electrode 106. The manufacturing method and the material for the mask 310 may be, for example the same as those explained with reference to FIG. 2B. Then, as shown in FIG. 7C, a portion, which is not covered with the mask 310, of the second electrode 106 is made into a thin film by etching.

Figure 7D:
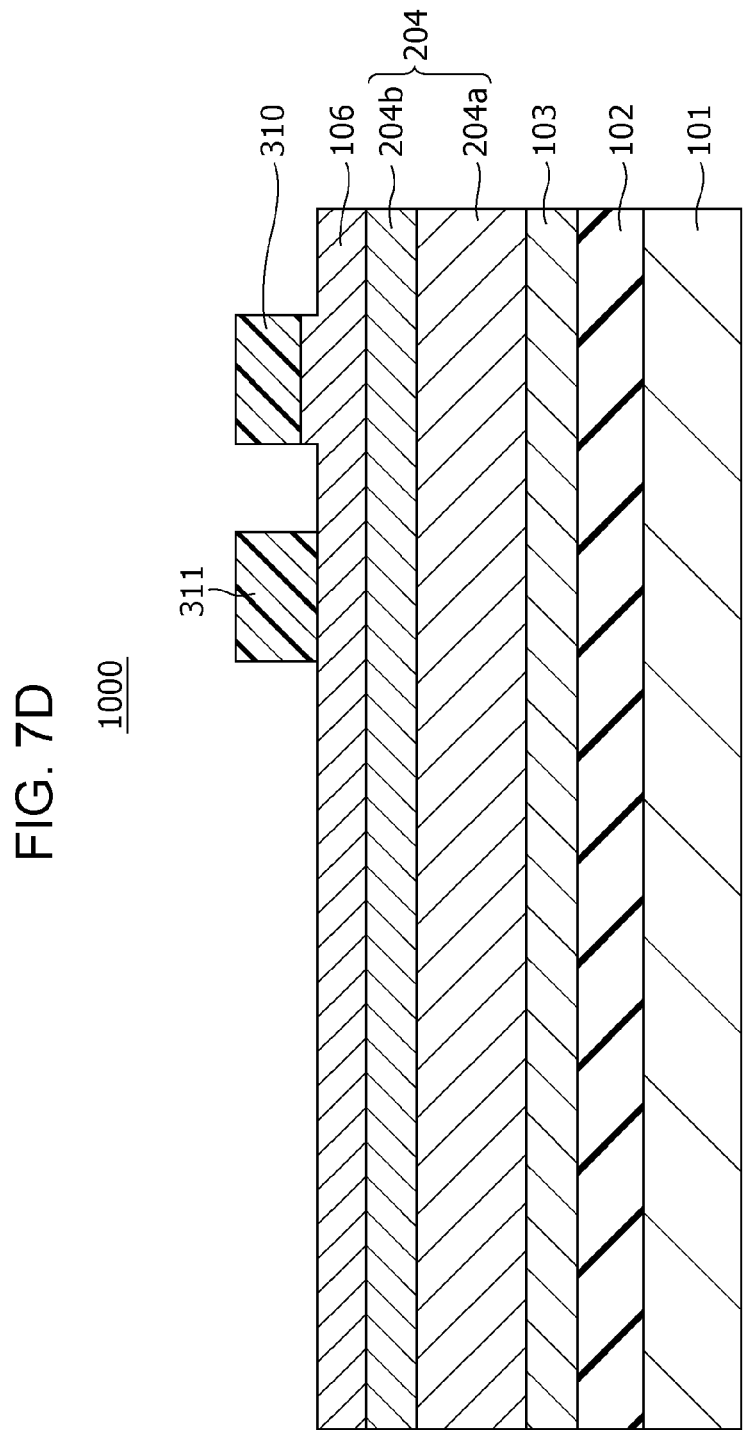
FIG. 7D is a sectional view showing an example of the method for manufacturing the gas sensor according to the first embodiment.

As shown in FIG. 7D, a mask 311 is formed on the second electrode 106. Then, as shown in FIG. 7E, a portion, which is not covered with the mask 310 nor the mask 311 of the second electrode 106, is further made into a thin film by etching.

As shown in FIG. 7F, a mask 312 is formed on the second electrode 106. Then, as shown in FIG. 7G, a portion, which is not covered with the mask 310, the mask 311, nor the mask 312 of the second electrode 106, is further made into a thin film by etching.

As shown in FIG. 7H, a mask 313 is formed on the second electrode 106. Then, as shown in FIG. 7I, a portion, which is not covered with the mask 310, the mask 311, the mask 312, nor the mask 313 of the second electrode 106, is further made into a thin film by etching.

Figure 7J:
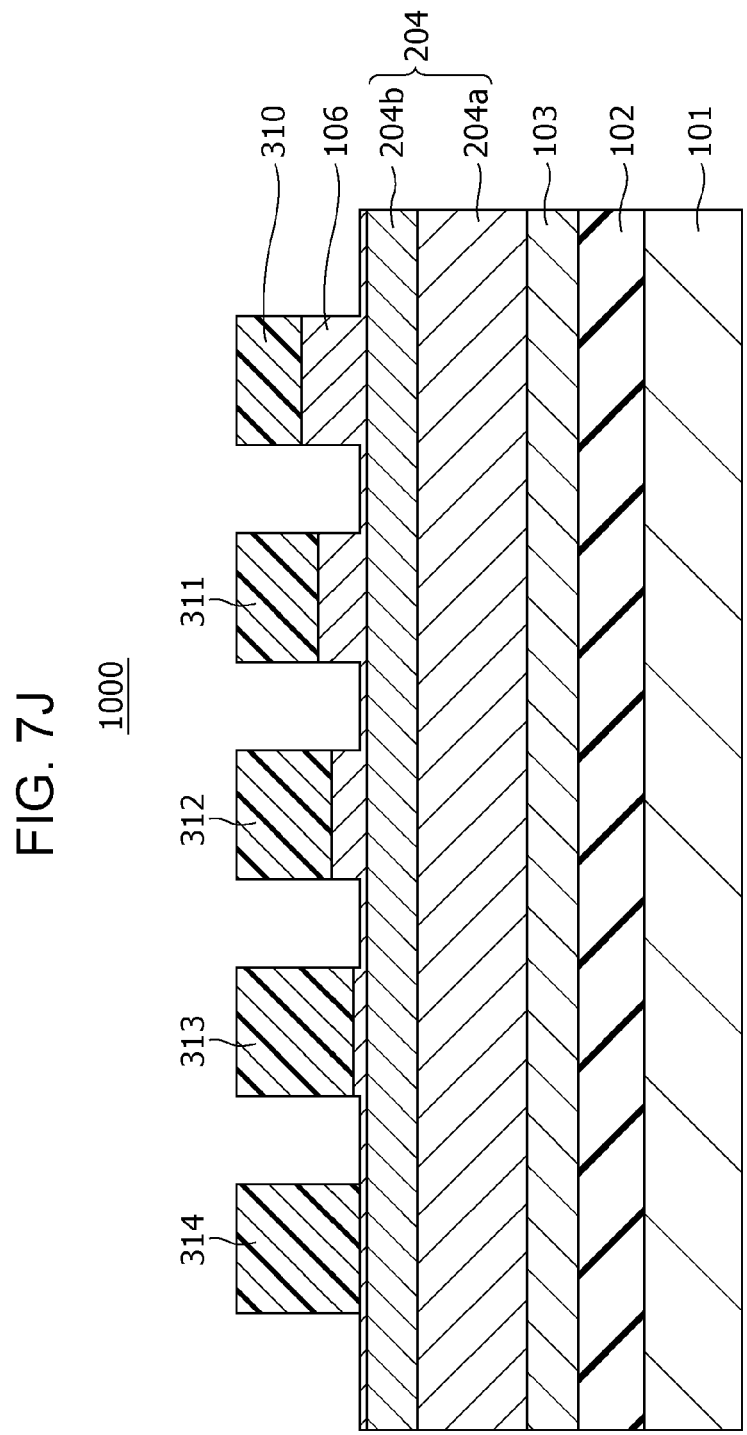
FIG. 7J is a sectional view showing an example of the method for manufacturing the gas sensor according to the first embodiment.
Figure 7K:
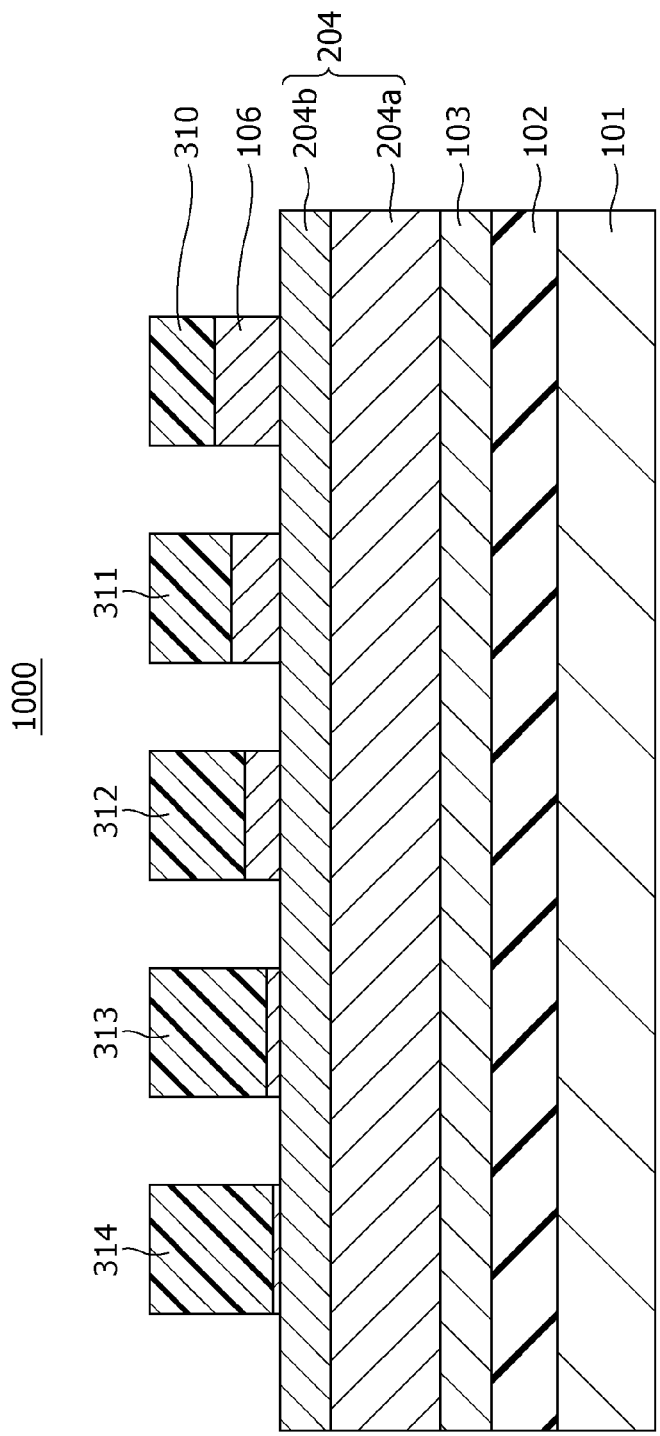
FIG. 7K is a sectional view showing an example of the method for manufacturing the gas sensor according to the first embodiment.

As shown in FIG. 7J, a mask 314 is formed on the second electrode 106. Then, as shown in FIG. 7K, a portion, which is not covered with the mask 310, the mask 311, the mask 312, the mask 313, nor the mask 314 of the second electrode 106, is removed by etching.

As shown in FIG. 7L, the masks 310, 311, 312, 313, and 314 are removed.

Thereafter, the insulation film 107 having the opening 107a, the via 108, and the wiring 109 are formed in the same manner as those described with reference to FIGS. 2D to 2G. Finally, the initial break voltage is applied to each of the gas detection elements 200 and, thereby, the local regions 105 are formed.

The gas sensor 1000 is completed through the above-described steps.

[3. Relationship Between Detection Sensitivity and Film Thickness of Second Electrode]

The relationship between the detection sensitivity of the gas detection element with respect to the hydrogen-containing gas and the film thickness of the second electrode will be described. In the following description, for the sake of simplifying the explanation, the case where each of detection cells constituting the gas sensor 1000 has the structure shown in FIG. 1A, that is, the case where each of the detection cells includes a single layer of the resistance film 104, will be explained. The following explanations also goes for the case where the gas sensor 1000 has the structure shown in FIG. 6, that is, the case where each of the detection cells includes the resistance film 204 which is a multilayer body.

Figure 8A:
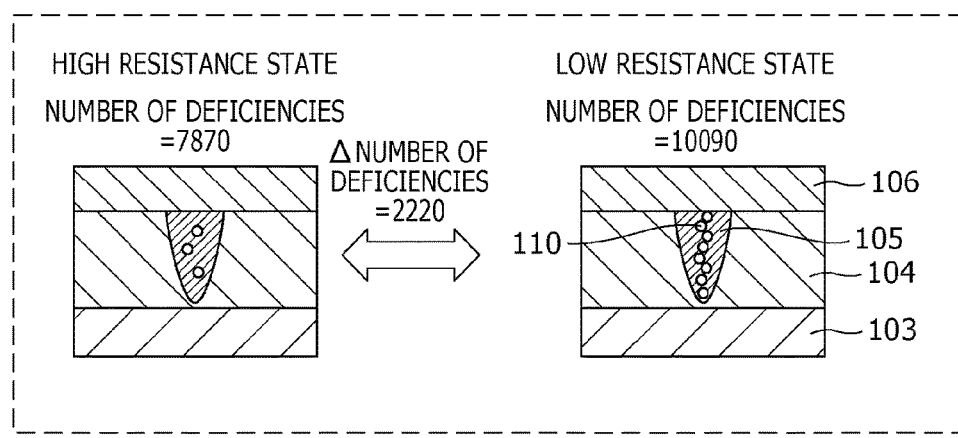
FIG. 8A is a schematic diagram showing an example of the resistance state and the oxygen deficiency state of a gas detection element according to the first embodiment.

FIG. 8A schematically shows the resistance state and the oxygen deficiency state of the gas detection element. The left side of FIG. 8A shows the gas detection element 100 in the high resistance state. The right side of FIG. 8A shows the gas detection element 100 in the low resistance state.

According to the simulation evaluation, it is estimated that in the case where the resistance value of the gas detection element 100 in the high resistance state is about 40 kΩ, about 7,870 of oxygen deficiencies 110 are present in the local region 105. At this time, the density of the oxygen deficiencies 110 is insufficient for forming a filament.

When hydrogen atoms pass through the second electrode 106 and reach the local region 105 in this state, these hydrogen atoms react with oxygen in the local region so as to generate new oxygen deficiencies 110. As a result, the gas detection element 100 makes a transition from the high resistance state to the low resistance state.

According to the simulation evaluation, it is estimated that in the case where the resistance value of the gas detection element 100 in the low resistance state is about 4 kΩ, about 10,090 of oxygen deficiencies 110 are present in the local region 105. At this time, the density of the oxygen deficiencies 110 is sufficient for forming a filament.

Therefore, in order that the hydrogen-containing gas sufficiently decrease the resistance value (for example, by about one order of magnitude) of the gas detection element 100, nearly the same number of hydrogen atoms as the increased number of oxygen deficiencies 110 (for example, 10,090−7,870=2,220), which is required for decreasing the resistance value described above, have to reach the local region 105.

Figure 8B:
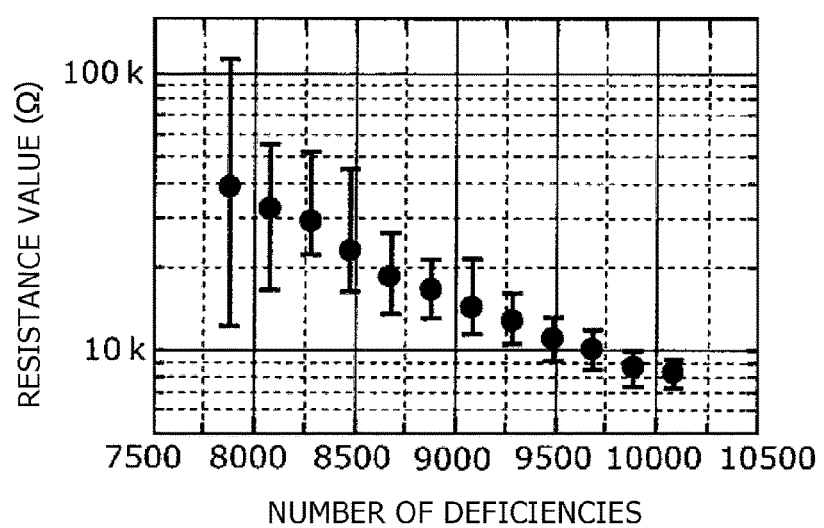
FIG. 8B is a diagram showing an example of the relationship between the resistance value and the number of deficiencies of the gas detection element according to the first embodiment.

FIG. 8B is a diagram showing an example of the relationship between the resistance value and the number of deficiencies present in the local region 105 of the gas detection element 100.

The number of hydrogen atoms that reach the local region 105 can be estimated on the basis of, for example, Formula (1). Regarding Formula (1), diffusion of hydrogen atoms in the second electrode 106 is taken into consideration.

$$n = N_0 pA \sqrt{\frac{N_A k_B T}{2\pi M}} \, erfc\left(\frac{x}{2\sqrt{D_{pt}t}}\right) \quad (1)$$

Here, n represents the number of hydrogen atoms that reach the local region 105, x represents the film thickness of the second electrode 106, t represents the time, p represents the hydrogen concentration of the hydrogen-containing gas, and A represents the area of a surface, which is in contact with the second electrode 106, of the local region 105.

As shown in Formula (1), the number of hydrogen atoms that reach the local region 105 per unit time depends on the number of hydrogen atoms No contained in a gas in contact with the second electrode 106 and the film thickness x of the second electrode 106.

In the case where the second electrode 106 is platinum (Pt), each parameter of Formula (1) takes on the value shown in Table 1.

TABLE 1

| Parameter (1 atm 25° C.) | | Value | Unit |
| --- | --- | --- | --- |
| Number of gas molecules per unit volume | $N_O$ | 2.46 × 10$^{19}$ | cm$^{-3}$ |
| Hydrogen molecular weight | M | 2.02 | gmol$^{-1}$ |
| Diffusion coefficient of hydrogen in Pt (1), (2) | $D_{pt}$ | 1.45 × 10$^{12}$ $\sqrt{P_{H2}}$ | cm$^{-2}$s$^{-1}$ |
| Avogadro constant | $N_A$ | 6.02 × 10$^{23}$ | |
| Boltzmann constant | $k_B$ | 1.38 × 10$^{-23}$ | JK$^{-1}$ |

(1) S. Uemiya, Topics in Catalysis 29, 79, 2004
(2) J. D. Fast Interaction of Metals and Gasses 1965

Figure 9A:
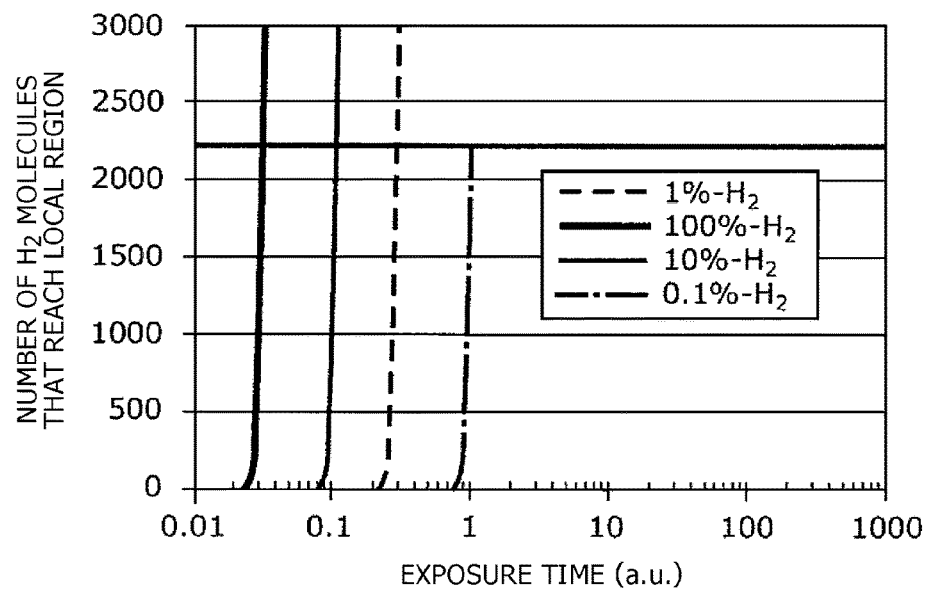
FIG. 9A is a diagram showing an example of the relationship between the time of exposure of the element to the hydrogen-containing gas and the number of hydrogen atoms that reach the local region in the gas detection element according to the first embodiment.

FIG. 9A shows an example of the relationship between the time of exposure of the gas detection element 100 to the hydrogen-containing gas and the number of hydrogen molecules that reach the local region. Here, the second electrode 106 was platinum and the thickness thereof was set to be 18.6 nm. FIG. 9A shows a graph in which the hydrogen concentration was 0.1%, 1%, 10%, and 100%.

As shown in FIG. 9A, the number of hydrogen molecules that reach the local region 105 sharply increased when a certain critical time elapsed. The critical time decreased as the hydrogen concentration increased.

Figure 9B:
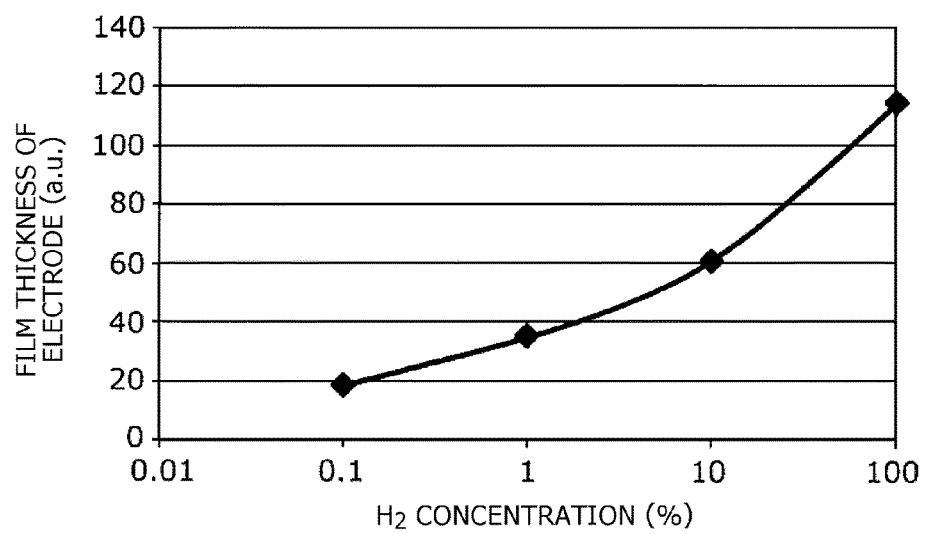
FIG. 9B is a diagram showing an example of the relationship between the hydrogen concentration of the hydrogen-containing gas and the film thickness of a second electrode which can detect a hydrogen-containing gas 1 second after start of introduction of the hydrogen-containing gas.

FIG. 9B shows the correlation between the hydrogen concentration and the film thickness of the platinum electrode under the condition in which 2,220 hydrogen molecules reach the local region 105 at the point in time when 1 second has elapsed from start of exposure to hydrogen gas. As is clear from FIG. 9B, as the hydrogen concentration is low, the film thickness of the second electrode 106 is small. In other words, in order to detect hydrogen in a gas having a low hydrogen concentration, the second electrode 106 is required to have a small film thickness.

As is clear from these investigations, the detection sensitivity of the gas detection element 100 with respect to the hydrogen-containing gas is set by adjusting the film thickness of the second electrode 106. In other words, the response time of resistance variation of the gas detection element 100 with respect to the hydrogen-containing gas can be set by adjusting the film thickness of the second electrode 106.

In the present disclosure, the term "response time" refers to the time period from exposure of the detection cell (that is, gas detection element) to the hydrogen-containing gas to a significant variation of the resistance value of the detection cell. The term "significant variation" refers to a decrease in the resistance value of the detection cell to a level lower than a predetermined level for determination.

A plurality of gas detection elements 100 exhibiting different response times of resistance variation with respect to the hydrogen-containing gas have, for example, the following properties. (1) The hydrogen concentrations in the hydrogen-containing gas required for generating a predetermined magnitude of resistance variation of the plurality of gas detection elements 100 when exposed to the hydrogen-containing gas for predetermined time periods are different in every gas detection element 100. (2) The exposure times required for significantly vary the resistance values of the plurality of gas detection elements 100 when exposed to the hydrogen-containing gas having a predetermined hydrogen concentration are different in every gas detection element 100.

[4. Determination of Hydrogen Concentration]

Figure 10A:
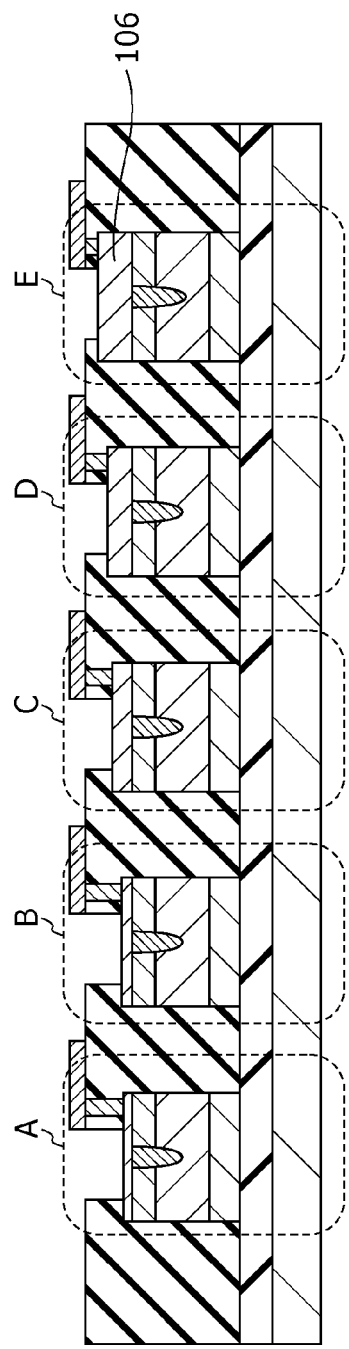
FIG. 10A is a sectional view showing an example of a gas sensor according to the first embodiment.
Figure 10B:
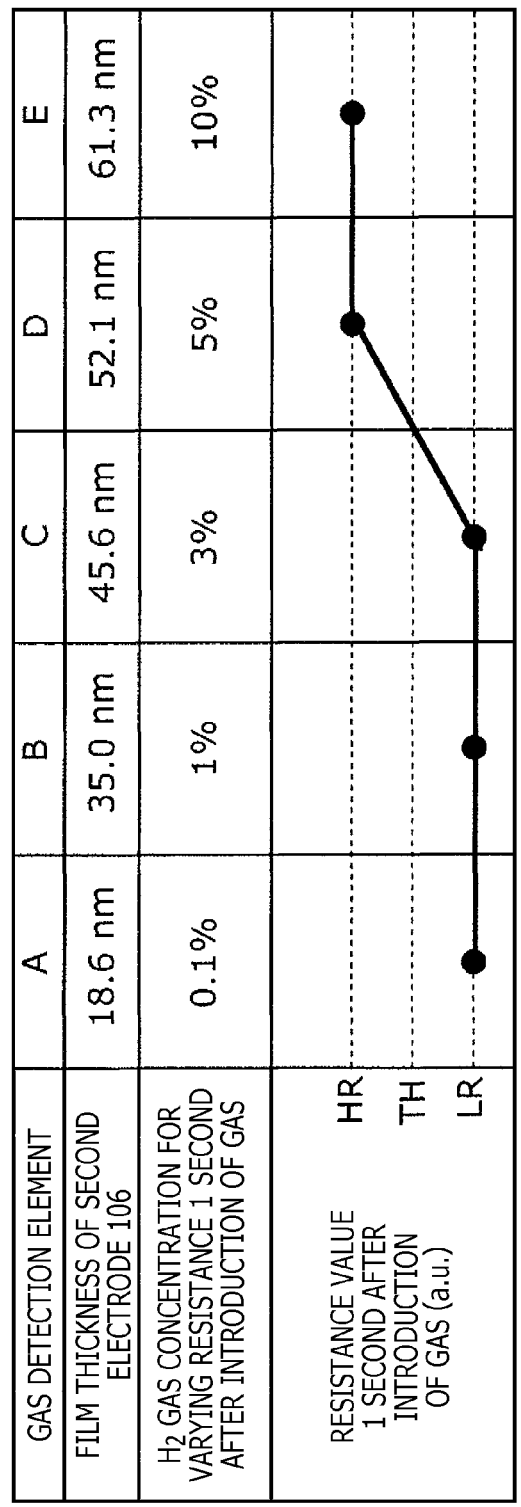
FIG. 10B is a diagram showing an example of the results of determination of the hydrogen concentration by the use of gas detection elements shown in FIG. 10A.

FIG. 10A shows the plurality of detection cells (that is, gas detection elements 100) included in the gas sensor 1000 shown in FIG. 6 and represented by reference numerals A to E. FIG. 10B shows the film thicknesses of the second electrodes 106 in the detection cells A to E shown in FIG. 10A and hydrogen concentrations required for decreasing the resistance variation by about one order of magnitude 1 second after introduction of the hydrogen-containing gas.

The film thicknesses of the second electrodes 106 of the detection cells A, B, C, D, and E were set to be 18.6 nm, 35.0 nm, 45.6 nm, 52.1 nm, and 61.3 nm, respectively. At this time, the resistance values of the detection cells A, B, C, D, and E decrease by about one order of magnitude 1 second after introduction of the hydrogen-containing gases having hydrogen concentrations of 0.1%, 1%, 3%, 5%, and 10%, respectively. These values of the film thicknesses of the second electrode 106 and the hydrogen concentrations were estimated by simulation.

The lowest row in FIG. 10B shows the resistance values of the detection cells A to E 1 second after introduction of the hydrogen-containing gas having some hydrogen concentration into the detection cells A to E. In this example, the resistance values of the detection cells A to E were set to be HR before introduction of the hydrogen-containing gas.

As shown in the lowest row in FIG. 10B, at the point in time when 1 second had elapsed from introduction of the hydrogen-containing gas, the resistance values of the detection cells A, B, and C decreased from HR to LR, and the resistance values of the detection cells D and E remained HR. In this case, it is determined that the concentration of the introduced hydrogen-containing gas was within the range of 3% or more and less than 5%.

As another example, although not shown in the drawing, it is assumed that when 1 second had elapsed from introduction of the hydrogen-containing gas, the resistance values of the detection cells A, B, C, and D decrease from HR to LR, and the resistance value of only the detection cell E remains HR. In this case, it is determined that the concentration of the introduced hydrogen-containing gas is within the range of 5% or more and less than 10%.

In this regard, whether a resistance variation of a detection cell occurred or not may be determined by whether the resistance value of the detection cell was lower than the threshold value TH set in advance or not. For example, the threshold value TH may be set to be between the resistance value before the resistance variation and the resistance value after the resistance variation. The resistance value of the detection cell may be measured by measuring the value of a current that passes when a predetermined voltage is applied to the detection cell.

Figure 11A:
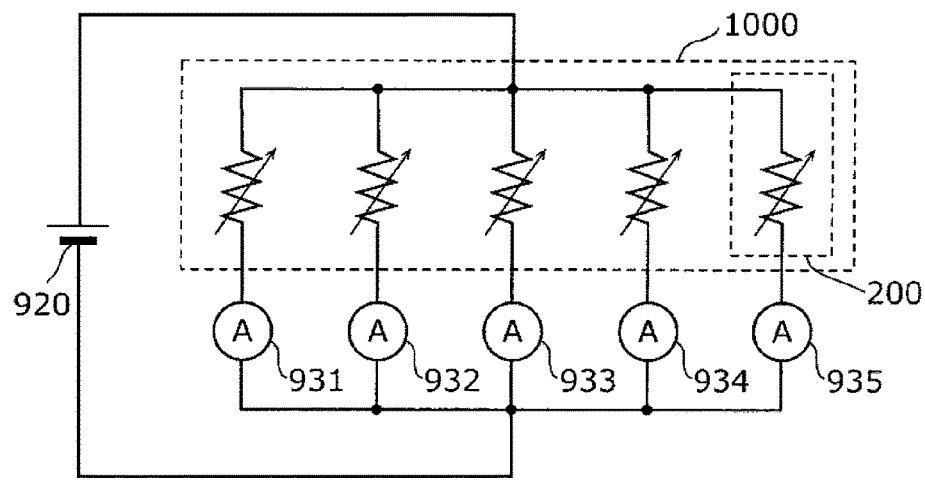
FIG. 11A is a circuit diagram showing an example of a hydrogen concentration determination circuit according to the first embodiment.

FIG. 11A is a circuit diagram showing an example of a gas sensor 1001 for determining the hydrogen concentration.

The gas sensor 1001 shown in FIG. 11A includes current measuring instruments 931 to 935 connected to the respective detection cells (that is, gas detection elements 200) and a power supply circuit 920 in addition to the gas sensor 1000 shown in FIG. 6. In the gas sensor 1001, the portion including the current measuring instruments 931 to 935 and the power supply circuit 920 is an example of the "measurement circuit" according to the present disclosure.

Each of the current measuring instruments 931 to 935 includes a comparator which compares the value of a current passing through the corresponding detection cell and a predetermined threshold value and which outputs the result thereof. This threshold value serves as a reference for determining whether the corresponding detection cell is in the high resistance state or in the low resistance state.

The plurality of detection cells are set to be in the high resistance state before the hydrogen-containing gas is measured. In this state, the power supply circuit 920 applies a predetermined voltage between the first electrode 103 and the second electrode 106 of each of the plurality of detection cells. Consequently, currents passing through the plurality of detection cells are monitored by the current measuring instruments 931 to 935.

In this state, the plurality of detection cells are exposed to a gas which is the target of the inspection. In the case where the gas is a hydrogen-containing gas, the resistance value of each of the detection cells decreases with the response time in accordance with the hydrogen concentration of the gas and the film thickness of the second electrode 106. The response times are different in every detection cell because the film thicknesses of the second electrodes 106 are different in every detection cell.

When the resistance value of a detection cell decreases, the value of current passing through the current measuring instrument connected to this detection cell (for example, the current measuring instrument 931) increases. The comparator in each of the current measuring instruments 931 to 935 outputs a signal indicating detection of the hydrogen-containing gas when the current value exceeds the threshold value. This signal is output to, for example, the determination circuit (not shown in the drawing) in the gas sensor 1001.

The response times are different in every detection cell. Therefore, when a predetermined time (for example, 1 second) has elapsed from start of introduction of the hydrogen-containing gas, for example, some of the current measuring instruments 931 to 935 have detected the hydrogen-containing gas and the remainder has not yet detected the hydrogen-containing gas. Consequently, the determination circuit (not shown in the drawing) can determine the hydrogen concentration on the basis of the signals input from the current measuring instruments 931 to 935. The resolution of the gas sensor 1001 with respect to the hydrogen concentration depends on differences in the film thicknesses of the second electrodes 106 in the plurality of detection cells.

Figure 11B:
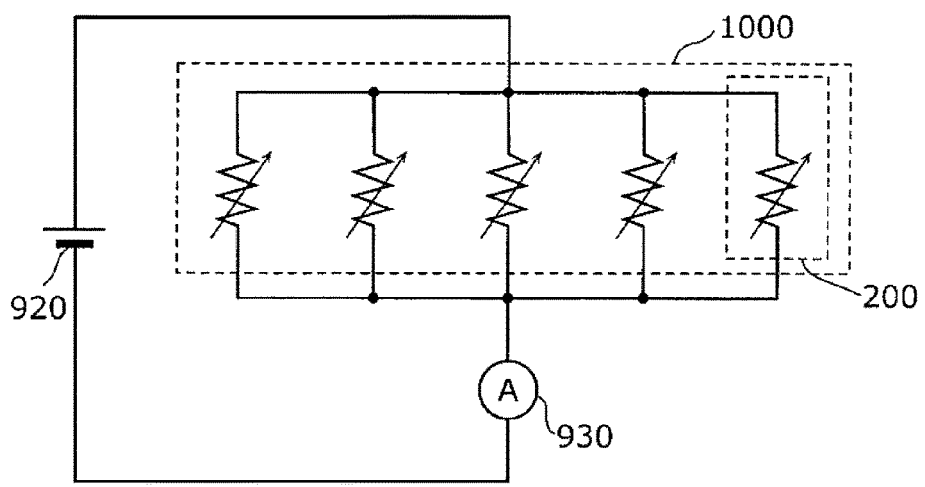
FIG. 11B is a circuit diagram showing another example of a hydrogen concentration determination circuit according to the first embodiment.

FIG. 11B is a circuit diagram showing an example of a gas sensor 1002 for determining the hydrogen concentration. The gas sensor shown in FIG. 11B includes a current measuring instrument 930 connected to a plurality of detection cells and a power supply circuit 920 in addition to the gas sensor 1000 shown in FIG. 6. In the gas sensor 1002, the portion including the current measuring instrument 930 and the power supply circuit 920 is an example of the "measurement circuit" according to the present disclosure.

The gas sensor 1002 is different from the gas sensor 1001 in the points described below.

The current measuring instrument 930 monitors the sum total of currents passing through the plurality of detection cells as a synthetic current. The current measuring instrument 930 includes, for example, a comparator which compares the synthetic current with each of the plurality of threshold values and which outputs the results. These threshold values are set so as to determine how many detection cells among the plurality of detection cells varied from the high resistance state to the low resistance state. Therefore, gas sensor 1002 can specify the number of the detection cells, which detected the hydrogen-containing gas on the basis of the synthetic current when a predetermined time (for example, 1 second) elapsed from start of introduction of the hydrogen-containing gas, and can determine the hydrogen concentration in the hydrogen-containing gas in accordance with the number of the detection cells.

The start of introduction of the hydrogen-containing gas may be detected by the gas sensor 1001 or the gas sensor 1002. For example, a point in time when the detection cell having the highest sensitivity detects the hydrogen-containing gas may be set to be the point in time when the introduction of the hydrogen-containing gas is started. The gas sensor 1001 or the gas sensor 1002 may be set as described above so as to be used in an environment in which, for example, the hydrogen-containing gas is intentionally not introduced.

The power supply circuit 920 may continuously apply a predetermined voltage between the first electrode 103 and the second electrode 106 of each of the plurality of detection cells. Consequently, variation of the hydrogen concentration in the hydrogen-containing gas can be detected in a short time while the gas sensor 1001 or the gas sensor 1002 is operated with a low power consumption.

Here, the example in which values of the currents passing through the plurality of detection cells are measured has been explained. This is an example of "measuring the resistance value between the first electrode and the second electrode in each of the plurality of detection cells".

Second Embodiment

A gas sensor according to a second embodiment will be described. Regarding the explanations of the second embodiment, explanations of the items common to those of the reference embodiment and/or the first embodiment may be omitted.

[1. Configuration of Gas Sensor]

Figure 12:
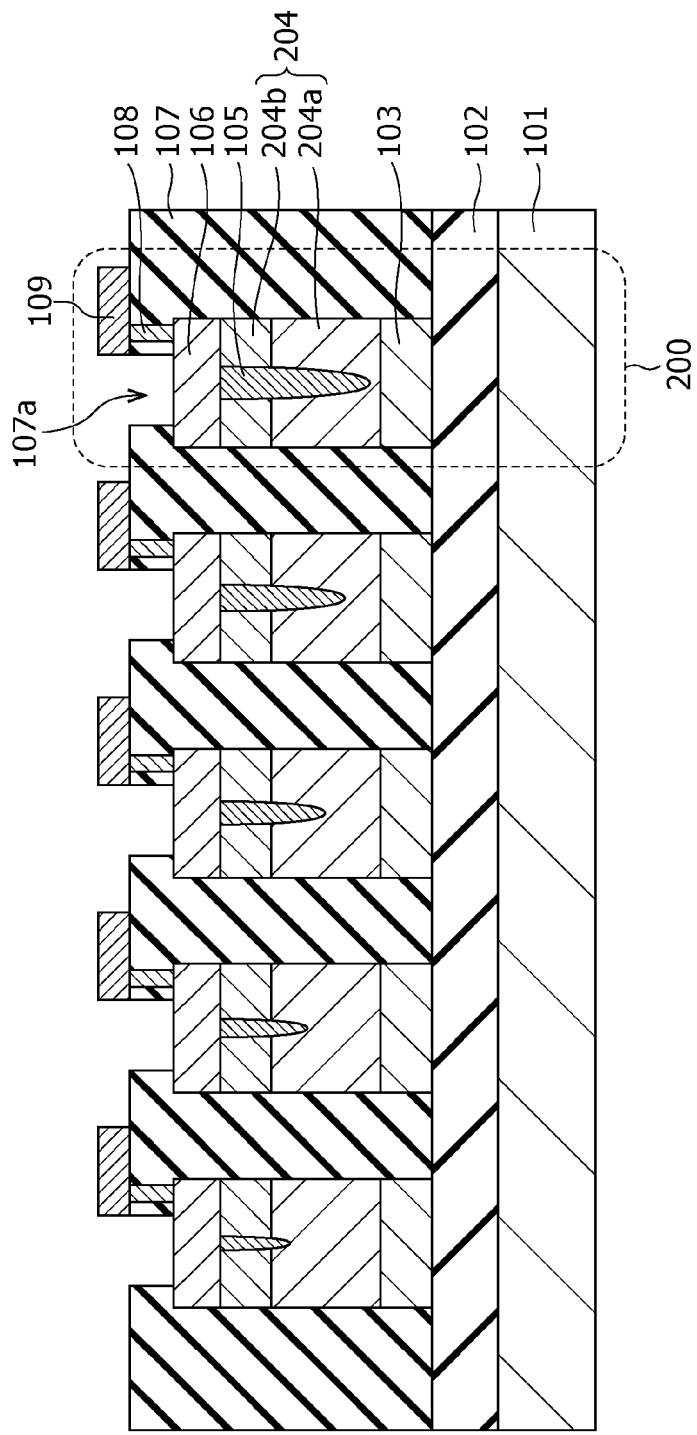
FIG. 12 is a sectional view showing an example of a gas sensor according to a second embodiment.

FIG. 12 is a sectional view showing a configuration example of a gas sensor 2000 according to the second embodiment. The gas sensor 2000 includes a plurality of gas detection elements 200 as detection cells. Each of the plurality of gas detection elements 200 has, for example, the same structure as the structure of the gas detection element 200 explained in the reference embodiment. In the gas sensor 2000 shown in FIG. 12, five gas detection elements 200 are arranged. The diameters of local regions of the five gas detection elements 200 are different from each other.

The number of the gas detection elements 200 included in the gas sensor 2000 is not limited to five. The gas sensor 2000 may include, for example, a plurality of gas detection element 100 explained in the reference embodiment in place of the plurality of gas detection elements 200. Each of the substrates 101 and the insulation film 102 in the gas sensor 2000 may be common to the plurality of gas detection elements 200. Likewise, the insulation film 107 of the gas sensor 2000 may be a common layer covering the plurality of first electrodes 103, the plurality of resistance films 204, and the plurality of second electrodes 106 of the plurality of gas detection elements 200.

In FIG. 12, all the diameters of the local regions 105 of five gas detection elements 200 are different from each other. However, at least two of diameters of the local regions 105 of the plurality of gas detection elements 200 may take on values different from each other. The dimensional relationship between the diameters of the local regions 105 is examined by performing EBAC analysis from the upper surface of the gas sensor 2000.

[2. Method for Manufacturing Gas Sensor]

Regarding a method for manufacturing the gas sensor 2000, basically, the same manufacturing method as the manufacturing method explained with reference to FIG. 2A to FIG. 2G may be used. However, in the method for manufacturing the gas sensor 2000, in order to make the diameters of the local regions 105 different in every gas detection element 200, initial break voltages different in every gas detection element 200 are applied.

Figure 13:
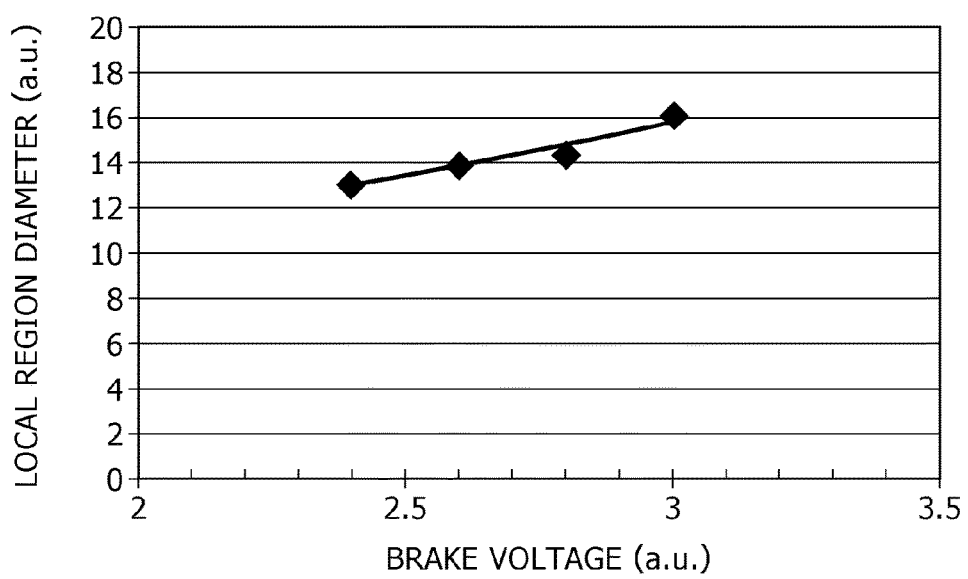
FIG. 13 is a diagram showing an example of the relationship between the initial break voltage and the diameter of a local region formed in a gas detection element according to the second embodiment.

FIG. 13 shows an example of the relationship between the initial break voltage and the diameter of the local region. As shown in FIG. 13, the diameter of the local regions 105 increases as the initial break voltage value increases.

[3. Relationship Between Detection Sensitivity and Diameter of Local Region]

The relationship between the detection sensitivity of the gas detection element with respect to the hydrogen-containing gas and the diameter of the local region will be described. In the following description, for the sake of simplifying the explanation, the case where each of detection cells constituting the gas sensor 2000 has the structure shown in FIG. 1A, that is, the case where each of the detection cells includes a single layer of the resistance film 104, will be explained. The following explanations also goes for the case where the gas sensor 2000 has the structure shown in FIG. 6, that is, the case where each of the detection cells includes the resistance film 204 which is a multilayer body.

As described in the reference embodiment, the resistance value of the gas detection element 100 decreases by bonding of hydrogen atoms to oxygen in the local region 105. Therefore, the easiness in a decrease in the resistance value (that is, detection sensitivity) of the gas detection element depends on the easiness in bonding between hydrogen atoms and oxygen in the local region 105.

Figure 14A:
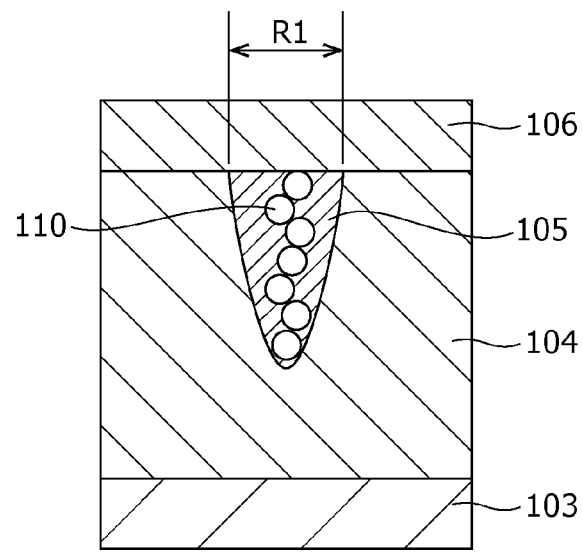
FIG. 14A is a schematic diagram showing an example of an oxygen deficiency state of the gas detection element according to the second embodiment.
Figure 14B:
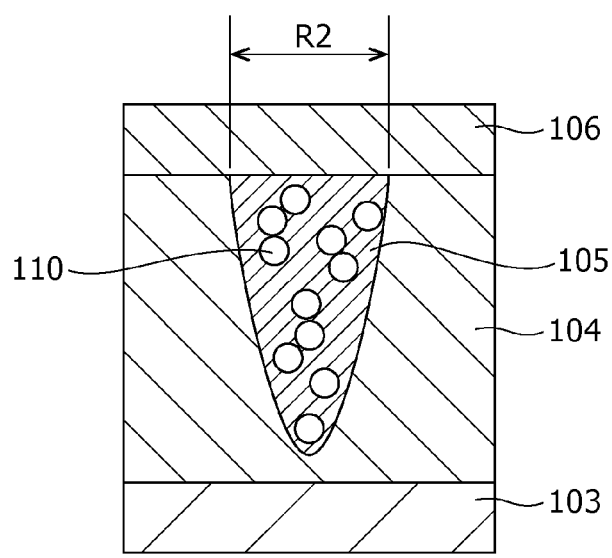
FIG. 14B is a schematic diagram showing another example of an oxygen deficiency state of the gas detection element according to the second embodiment.

FIG. 14A schematically shows oxygen deficiencies 110 in the local region 105 having a diameter of R1. FIG. 14B schematically shows the state of oxygen deficiencies 110 in the local region 105 having a diameter of R2 (>R1).

Hydrogen atoms pass through the cross section of the local region 105 (cross-sectional area A) and spreads in a predetermined region (volume V). Assuming that the cross-sectional area A is proportional to the square of the diameter R of the local region 105 and the volume V is proportional to the cube of the diameter of the local region 105, the cross-sectional area per volume (A/V) of the local region 105 is inversely proportional to the diameter of the local region 105. According to Formula (1) above, the number n of hydrogen atoms that reach the local region 105 is proportional to the cross-sectional area A of the local region 105. Therefore, the number of hydrogen atoms per unit volume (n/V) is inversely proportional to the diameter of the local region 105. That is, as the diameter of the local region 105 decreases, the density of hydrogen atoms in the local region 105 increases. The oxygen deficiencies are generated by a reaction between hydrogen and oxygen. Consequently, as the density of hydrogen atoms increases, the density of oxygen deficiencies increases, and the resistance value of the local region 105 easily decreases. In other words, as the diameter of the local region 105 decreases, the detection sensitivity with respect to the hydrogen-containing gas increases.

FIG. 13 shows the relationship between the initial break voltages applied to Samples (i) to (iv) and the diameters of the resulting local regions 105. The initial break voltages of 2.4 V, 2.6 V, 2.8 V, and 3.0 V were applied to Samples (i) to (iv), respectively. The diameters of the local regions 105 of Samples (i) to (iv) were 13.0, 13.8, 14.2, and 16.0 (a.u.), respectively.

According to these examples, the diameters of the local regions 105 of Samples (ii), (iii), and (iv) were about 1.06 times, about 1.09 times, and about 1.23 times, respectively, the diameter of the local region 105 of Sample (i). Therefore, the densities of oxygen deficiencies of the local regions 105 of Samples (ii), (iii), and (iv) are estimated to be about 94% (=1/1.06), about 92% (=1/1.09), and about 81% (=1/1.23), respectively, of the density of oxygen deficiencies of the local region 105 of Sample (i). Consequently, it is considered that the detection sensitivities of Samples (i), (ii), (iii), and (iv) decrease in this order.

[4. Determination of Hydrogen Concentration]

The gas sensor 2000 can determine the hydrogen concentration of the hydrogen-containing gas.

Specifically, in the gas sensors 1001 and 1002 explained in the first embodiment, the gas sensor 1000 can be replaced with the gas sensor 2000. The operations of the gas sensors 1001 and 1002 are as explained in the first embodiment.

Overview of Embodiments

In one aspect, the techniques disclosed here feature a gas sensor including a plurality of gas detection elements having gas detection sensitivities different from each other, wherein each of the plurality of gas detection elements includes a first electrode and a second electrode, which are arranged such that the principal surfaces are opposed to each other, a metal oxide layer arranged so as to be in contact with the principal surface of the first electrode and the principal surface of the second electrode, and an insulation film covering the first electrode, the second electrode, and the metal oxide layer, at least part of the other surface, which is opposite to the principal surface, of the second electrode is exposed without being covered with the insulation film, a local region, which is in contact with the second electrode and which has a degree of oxygen deficiency higher than that of the metal oxide layer, is included inside the metal oxide layer, and in each of the plurality of gas detection elements, the resistance value of the metal oxide layer decreases in the case where the second electrode comes into contact with a gas containing gas molecules having hydrogen atoms.

According to this configuration, a current passing between the first electrode and the second electrode concentrates on the local region having a high degree of oxygen deficiency. As a result, the temperature of the local region can be raised with a small amount of current. Consequently, a hydrogen-containing gas can be detected without heating with a heater by utilizing self-heating and gas sensitivity of the local region formed inside the metal oxide layer and, thereby, a gas sensor having an excellent power saving function is obtained.

In the plurality of gas detection elements, the resistance values between the first electrode and the second electrode decrease with detection sensitivities different from each other and, thereby, the range of hydrogen concentration in the gas can be determined.

In each of the plurality of gas detection elements, the second electrode may be composed of a material having a catalytic function to dissociate the hydrogen atoms from the gas molecules.

In each of the plurality of gas detection elements, the local region may generate heat because of the current passing between the first electrode and the second electrode, hydrogen atoms may be thereby dissociated from the gas molecules in the portion, which is in contact with the local region, of the second electrode, and the dissociated hydrogen atoms may bond to oxygen atoms in the local region of the metal oxide layer so as to decrease the resistance value of the metal oxide layer.

According to this configuration, in the case where gas molecules containing hydrogen atoms come into contact with the second electrode, hydrogen atoms are dissociated from the gas molecules, and the dissociated hydrogen atoms diffuse in the second electrode so as to reach the local region. Then, the hydrogen atoms bond to oxygen in the metal oxide present in the local region so as to form water ($H_2O$) and, thereby, the degree of oxygen deficiency of the local region further increases. Consequently, the current easily passes through the local region and the resistance between the first electrode and the second electrode decreases.

In the case where gas molecules containing hydrogen atoms become not present in the vicinity of the surface of the second electrode, $H_2O$ in the local region is decomposed by a chemical reaction with the oxygen-deficient metal oxide. The resulting hydrogen atoms diffuse in the second electrode, reach the surface of the second electrode, form hydrogen molecules there, and hydrogen molecules are released into the air. On the other hand, oxygen atoms bond to the oxygen-deficient metal oxide and the degree of oxygen deficiency of the local region is lowered. Consequently, a current does not easily pass through the local region and the resistance between the first electrode and the second electrode increases.

The thicknesses of the second electrodes of the plurality of gas detection elements may be different from each other.

According to this configuration, the film thicknesses of the second electrodes are made to be different in every gas detection element and, thereby, the plurality of gas detection elements having gas detection sensitivities different from each other are formed.

The diameters of the local regions of the plurality of gas detection elements may be different from each other.

According to this configuration, the diameters of the local regions are made to be different in every gas detection element and, thereby, the plurality of gas detection elements having gas detection sensitivities different from each other are formed.

In each of the plurality of gas detection elements, the metal oxide layer may make an inverse transition between a high resistance state and a low resistance state, in which the resistance value is lower than the resistance value in the high resistance state, on the basis of a voltage applied between the first electrode and the second electrode.

According to this configuration, the metal oxide layer is set to be in the electrically high resistance state in advance and, thereby, a decrease in the resistance value of the metal oxide layer can be more clearly detected. Therefore, the range of hydrogen concentration can be more reliably determined.

In each of the plurality of gas detection elements, the metal oxide layer may be formed by stacking a first metal oxide layer composed of a first metal oxide and a second metal oxide layer composed of a second metal oxide having a degree of oxygen deficiency lower than that of the first metal oxide, wherein the first metal oxide layer is in contact with the first electrode, the second metal oxide layer is in contact with the second electrode, and the local region may be formed so as to penetrate at least the second metal oxide layer and to come into contact with the second electrode and may have a degree of oxygen deficiency higher than that of the second metal oxide layer.

In each of the plurality of gas detection elements, the second electrode may be composed of platinum or palladium.

In each of the plurality of gas detection elements, each of the first metal oxide and the second metal oxide may be a transition metal oxide or an aluminum oxide.

In each of the plurality of gas detection elements, the transition metal oxide may be any one of a tantalum oxide, a hafnium oxide, and a zirconium oxide.

According to these configurations, a gas sensor having excellent resistance variation characteristics and high reliability is obtained by adopting appropriate structure and material.

Further, a measurement circuit may be included for measuring currents passing through the plurality of gas detection elements when a predetermined voltage is applied between the first electrode and the second electrode of each of the plurality of gas detection elements.

According to this configuration, the range of hydrogen concentration in a gas can be determined by specifying the resistance states of the plurality of gas detection elements on the basis of the current measured with the measurement circuit.

Further, a power supply circuit may be included for continuously applying a predetermined voltage between the first electrode and the second electrode of each of the plurality of gas detection elements.

According to this configuration, the range of hydrogen concentration in the hydrogen-containing gas can be determined in a short time while an excellent power saving function of the gas sensor is utilized.

A method for determining a hydrogen concentration according to an aspect of the present disclosure determines the range of hydrogen concentration of the hydrogen-containing gas by exposing a gas sensor, which includes a plurality of gas detection elements having gas detection sensitivities different from each other, to the hydrogen-containing gas and measuring the resistance values of the plurality of gas detection elements after a lapse of a predetermined time from start of exposure.

According to this method, the range of hydrogen concentration in the gas can be determined by utilizing the fact that the gas detection sensitivities are different in every gas detection element and specifying the gas detection elements with resistance values which have decreased after a lapse of the predetermined time and the gas detection elements with resistance values which have not decreased.

A method for determining a hydrogen concentration according to an aspect of the present disclosure determines the range of hydrogen concentration of the hydrogen-containing gas by exposing a gas sensor, which includes a plurality of gas detection elements having gas detection sensitivities different from each other, to a hydrogen-containing gas and measuring the resistance values of the plurality of gas detection elements after a lapse of the predetermined time from the point in time when the resistance value of the gas detection element having the highest gas detection sensitivity has decreased.

According to this method, even if the time in point when exposure of the gas sensor to the hydrogen-containing gas has started is not known, the range of hydrogen concentration in the gas can be determined on the basis of the point in time when the resistance value of the gas detection element having the highest gas detection sensitivity has decreased.

The gas sensor according to the present disclosure is particularly useful for gas detection for the purpose of determining the hydrogen concentration of a hydrogen-containing gas.

What is claimed is:
1. A gas sensor comprising:
an insulation layer; and
detection cells covered with the insulation layer and electrically connected in parallel with each other,
wherein each of the detection cells includes:
a first electrode;
a second electrode having a surface exposed from the insulation layer; and
a metal oxide layer disposed between the first electrode and the second electrode, the metal oxide layer including a bulk region and a local region surrounded by the bulk region, a degree of oxygen deficiency of the local region being higher than a degree of oxygen deficiency of the bulk region, and
wherein a film thickness of the second electrode is different in each of the detection cells.
2. The gas sensor according to claim 1,
wherein the film thickness of the second electrode having the maximum film thickness in the detection cells is 1.5 or more times the film thickness of the second electrode having the minimum film thickness.
3. The gas sensor according to claim 1,
wherein, in each of the detection cells, the local region faces the exposed surface across the second electrode.

4. The gas sensor according to claim 1,
wherein, in each of the detection cells, the metal oxide layer includes:
a first metal oxide layer being in direct contact with the first electrode, a degree of oxygen deficiency of the first metal oxide layer being higher than the degree of oxygen deficiency of the bulk region; and
a second metal oxide layer being in direct contact with the second electrode, the second metal oxide layer including the bulk region, and
in each of the detection cells, the local region is in direct contact with the second electrode and passes through the second metal oxide layer.
5. The gas sensor according to claim 1,
wherein, in each of the detection cells, the second electrode contains platinum or palladium.
6. The gas sensor according to claim 1, further comprising a measurement circuit configured to measure a resistance value between the first electrode and the second electrode in each of the detection cells.
7. The gas sensor according to claim 6, further comprising a determination circuit configured to determine a hydrogen concentration in the gas based on the resistance value measured in each of the detection cells.
8. The gas sensor according to claim 1, further comprising a power supply circuit configured to apply a voltage between the first electrode and the second electrode in each of the detection cells.
9. The gas sensor according to claim 1,
wherein, in each of the detection cells, the metal oxide layer contains at least one selected from a transition metal oxide and an aluminum oxide.
10. The gas sensor according to claim 9,
wherein the transition metal oxide is at least one selected from a tantalum oxide, a hafnium oxide, and a zirconium oxide.
11. The gas sensor according to claim 1,
wherein the second electrode is formed of the same material in each of the detection cells.
12. The gas sensor according to claim 1,
wherein the detection cells are arranged on the same substrate.
13. The gas sensor according to claim 1,
wherein the first electrode, the metal oxide layer, and the second electrode are stacked in this order in each of the detection cells.
14. The gas sensor according to claim 1,
wherein the insulation layer has an opening, through each of which the surface of the second electrode is exposed, and
a contour of the local region is located inside of a corresponding one of the openings, when viewed from a direction perpendicular to the exposed surface.
15. A gas sensor comprising:
an insulation layer; and
detection cells covered with the insulation layer and electrically connected in parallel with each other,
wherein each of the detection cells includes:
a first electrode;
a second electrode having a surface exposed from the insulation layer; and
a metal oxide layer disposed between the first electrode and the second electrode, the metal oxide layer including a bulk region and a local region surrounded by the bulk region, a degree of oxygen deficiency of the local region being higher than a degree of oxygen deficiency of the bulk region, and wherein a diameter of the local region is different in each of the detection cells.

16. A method for determining a hydrogen concentration with a gas sensor, comprising:
    measuring resistance values of detection cells at a same timing after the detection cells are exposed to a gas, and
    determining the hydrogen concentration of the gas based on the measured resistance values,
    wherein the gas sensor comprises:
        an insulation layer; and
        the detection cells covered with the insulation layer and electrically connected in parallel with each other,
    wherein each of the detection cells includes:
        a first electrode;
        a second electrode having a surface exposed from the insulation layer; and
        a metal oxide layer disposed between the first electrode and the second electrode, the metal oxide layer including a bulk region and a local region surrounded by the bulk region, a degree of oxygen deficiency of the local region being higher than a degree of oxygen deficiency of the bulk region, and
    wherein in each of the detection cells, a resistance value of the metal oxide layer decreases with a response time, which is different in each of the detection cells, when the gas containing a hydrogen atom comes into contact with the second electrodes.

17. The method according to claim 16, further comprising:
    detecting that the detection cells are exposed to the gas by detecting a decrease in at least one of the resistance values.

* * * * *